United States Patent [19]

Hilton et al.

[11] Patent Number: 5,452,416
[45] Date of Patent: Sep. 19, 1995

[54] AUTOMATED SYSTEM AND A METHOD FOR ORGANIZING, PRESENTING, AND MANIPULATING MEDICAL IMAGES

[75] Inventors: Wesley W. Hilton, Del Mar; Murray A. Reicher, Rancho Santa Fe; Dale Seegmiller, Solana Beach, all of Calif.

[73] Assignee: Dominator Radiology, Inc., San Diego, Calif.

[21] Appl. No.: 998,550

[22] Filed: Dec. 30, 1992

[51] Int. Cl.⁶ .......................... G06F 3/14; G06F 15/00
[52] U.S. Cl. .................................... 395/161; 395/157; 395/160; 395/124; 364/413.13; 364/413.22
[58] Field of Search ............... 395/161, 157, 155, 124, 395/160, 164, 153; 364/413.13, 413.14, 413.22

[56] References Cited

U.S. PATENT DOCUMENTS

| | | | |
|---|---|---|---|
| 4,642,621 | 2/1987 | Nemoto et al. | 364/413.22 X |
| 5,019,976 | 5/1991 | Chiu et al. | 364/413.13 |
| 5,099,846 | 3/1992 | Hardy | 364/413.13 X |
| 5,235,510 | 8/1993 | Yamada et al. | 364/413.22 X |
| 5,272,760 | 12/1993 | Echerer et al. | 382/6 |
| 5,274,759 | 12/1993 | Yoshioka | 395/161 X |
| 5,293,313 | 3/1994 | Cecil et al. | 364/413.22 |
| 5,313,567 | 5/1994 | Civanlar et al. | 395/124 |

OTHER PUBLICATIONS

Sanders et al., "Design and Implementation of a Clinical MSI Workstation", Proceedings of Computer-Based Medical Systems, IEEE Computer Society Press, Jun. 1992, pp. 138-146.

International Search Report, Issued by European Patent Office, Jun. 17, 1994, 3 sheets.

Proceedings of the 12th Annual International Conference of the IEEE Engineering in Medicine and Biology Society, IEEE Press New York, US, vol. 1/5, 1 Nov. 1990, Philadelphia, Pa., US, pp. 219-220.

Visual Computer, Springer Verlag, vol. 4, No. 2, 1988, Germany, pp. 98-108.

Sigbio Newsletter, vol. 12, No. 1, Feb. 1992, New York, US, pp. 10-22.

Primary Examiner—Raymond J. Bayerl
Attorney, Agent, or Firm—Baker, Maxham, Jester & Meador

[57] ABSTRACT

An automated system for organizing, presenting, and manipulating medical images includes a database in which the medical images are structured into groups, each group including one or more image series, each image series including an ordered sequence of images which illustrate incrementally registered aspects of an anatomical target. Image series are presented in their sequential order either in a monitor presentation format which displays each sequence in its entirety in a single monitor display container or which presents two or more image series, image-by-image, in adjacent presentation areas of a series display container. The system includes a plurality of monitors in which all monitors, save one, produce display containers for image series presentation. One monitor is reserved for displaying a working palette to which images of the image series displayed on the other monitors may be moved. The system activates a monitor in a plurality of monitors in response to movement of a cursor between monitors. An active monitor is indicated by presentation of a control panel. The system also provides heads-up presentation of control panel icons at a cursor location outside of the control panel by sequentially changing the shape of the cursor to the icon shapes for user selection.

16 Claims, 18 Drawing Sheets

AUTOMATED SYSTEM AND A METHOD FOR ORGANIZING, PRESENTING, AND MANIPULATING MEDICAL IMAGES

BACKGROUND OF THE INVENTION

The invention relates to the organization, presentation, and manipulation of images. More particularly, the invention provides efficient, user-friendly means and procedures for presenting images of anatomical structure and the like for examination.

The invention is also concerned with the activation of a display container for medical images in a context of a plurality of display containers, and with the presentation of icons without distracting the attention of a user from medical images which are being examined.

Magnetic resonance imaging (MRI) is an important, non-invasive imaging modality that is widely used by radiologists to examine internal anatomy to aid in the analysis of trauma and the diagnosis of disease. An MRI study provides a multi-planar representation of an anatomical target in the form of one or more image series. The images of a series may be parallel planar "slices" of the anatomical target which are incrementally registered along an imaging axis. Another imaging technology may produce image sequences which include non-parallel views that are incrementally registered about an axis of rotation or over a non-planar surface.

MRI technology is well understood. See, for example, MRI OF THE KNEE by Jerrol H. Mink, et al, Raven Press Ltd. (New York, N.Y. 1987) and the work by F.W. Wehrli, et al, entitled PARAMETERS DETERMINING THE OCCURRENCE OF NMR IMAGES published by the General Electric Company, Medical Systems Operations, in 1983.

In the prior art, the transparencies produced by an MRI system would be manually mounted in their series sequence on long light boxes where they would be read and annotated by radiologists. Following examination, the images would be physically stored in a patient's medical history folder. Recently, automated systems for archiving, retrieving, and presenting MRI images have been developed. In these systems, the images are conventionally converted to multi-bit, pixelated data representations which are formatted, stored, and retrieved using file management techniques. However, most conventional file management techniques are adapted for storage, retrieval, and presentation of documents, rather than images. Of course, these systems give even less consideration to the specialized requirements for storage and presentation of images showing internal anatomy.

Even the addition of a directly-manipulated user interface in conventional image storage and presentation systems does little to adapt these systems to the special needs of radiologists who must consider and manipulate many images in particular ways for special purposes. Furthermore, each radiologist has a highly personal mode of examination. For example, one radiologist may wish to examine a first sequence of transparencies in its entirety and then a second, related sequence before trying to correlate between individual images of the sequences. Another radiologist may wish to examine sequences in parallel by simultaneously considering images taken of the same anatomical plane under different conditions of exposure. Even currently-available database systems which have been adapted for storage and presentation of radiological images have not automated the presentation modalities of image series. Instead, a radiologist must provide for the individual retrieval and presentation of each and every stored image. In these systems, the images are individually identified and processed for storage and presentation without correlation to other images in their respective sequences. Furthermore, the existing systems do not provide for concurrent presentation of related image series.

Moreover, the currently available automated image storage systems are awkward and difficult to use, providing little in the way of means for direct manipulation of image presentation formats and images which are displayed for analysis.

SUMMARY OF THE INVENTION

Therefore, it is a primary objective of this invention to provide an automated system for storage, retrieval, and presentation of medical images which is especially adapted for the presentation of medical image sequences and which affords the user with a flexible and responsive set of functions that permit direct manipulation of the modes of image presentation and of the presented images themselves.

The invention is embodied in a computer display system which presents images of anatomical structure and the like for examination. The system includes the following combination:

a first display container including a first preselected number of substantially rectangular presentation areas in a substantially rectangular array;

a second display container including a second preselected number of substantially rectangular presentation areas in a substantially rectangular array;

an image database including a plurality of images of anatomical structure, the images being separated into image groups in which:

each image group is indexed by a unique group identification; and each image group is partitioned into one or more ordered image series, each ordered image series including a succession of images which illustrate incrementally registered aspects of an anatomical target, each image series being ordered by assignment to each image in the image series of a position in a respective monotonically changing sequence;

a mechanism connected to the image database and to the first and second display container and responsive to a group identification for displaying at least two image series of an image group indexed by the patient identification, wherein:

each image series is displayed in the order of its respective sequence in a respective display container such that each presentation area of the respective display container includes no more than one image; or, all of the image series are displayed in one display container and each image series is displayed one image at a time in the order of its respective sequence in a respective presentation area of the display container.

For direct manipulation of an interactive computer system with an output means for presenting visual displays wherein a user is presented with a visual display that includes a control display container (control panel), the invention further includes the following combination:

a first bounded display area presented by the output means, the first display area including:
 a control panel; and
 a plurality of icons displayed in the control panel;
a second bounded display area presented separately from the first display area by the output means;
a cursor mechanism connected to the output means for displaying and moving a cursor in a display area; and
a functional mechanism coupled to the first and second display areas and the to the cursor mechanism for presenting the control panel in the second display area in response to movement of the cursor from the first to the second display area.

Also, in an interactive computer system with an output means for presenting visual displays wherein a user is presented with a display that includes a directly-manipulated display container for presenting program output, the invention is embodied in a combination, in which:
 a cursor mechanism is connected to the output means for displaying and moving a cursor;
 a control display area is provided in the display in which a plurality of icons are displayed in a predetermined order;
 a pointing mechanism is provided, with connection to the cursor mechanism, for positioning the cursor and selecting icons in response to direct manual manipulation by a user; and
 an icon rotation mechanism is provided, with connection to the pointing mechanism and to the cursor mechanism, which responds to a position of the cursor inside the display container by changing the shape of the cursor at the position to the shape of an icon of the plurality of icons and by changing the shape of the cursor to the shapes of the other icons in the plurality of icons, such that the shape of the cursor is changed one shape at a time and in the predetermined order, in response to direct manual manipulation of the pointing mechanism.

BRIEF DESCRIPTION OF THE DRAWINGS

The invention, and its achievement of the above-stated objective, will be understood when the following detailed description is read in connection with the below-described drawings, in which.

DETAILED DESCRIPTION OF THE PREFERRED EMBODIMENT

The invention is intended to operate in connection with an image database which stores medical images for retrieval and presentation. Although the following description assumes that the images are data representations of pixelated images conventionally produced from the output of medical imaging technology such as MRI, X-ray, and CAT, this is not intended to limit such images to such sources. The inventors contemplate that the means and processes presented in this description would apply as well to a database of synthetically-created medical images.

In the preferred embodiment and best mode of this invention, the medical images are, in fact, those produced from an MRI apparatus. As is known, such an apparatus produces series, or sequences of images, which represent successively deeper planar slices of an anatomical target. In the examples given below, the anatomical target is the head of a human patient and it is assumed that three distinct series of images have been taken of the target. Two of these series are termed "axial". The images of an axial series represent parallel, planar images of cross-sectional anatomy taken along an imaginary vertical axis of the head. Each axial series is generated to emphasize particular anatomical features by varying parametric values of the MRI process. In this regard, see Chapter 1 of the Mink et al reference. The two axial series described in this embodiment are the well-known axial T1 and axial T2 sequences. The third series is a sagittal sequence in which the images are anatomical cross-sections lying in planes parallel to the median plane of the head.

Figure 1:
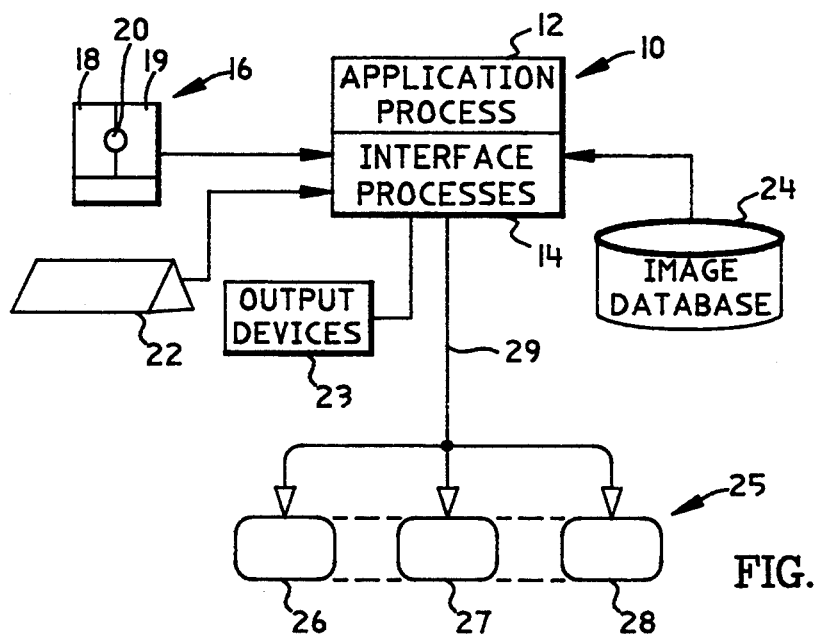
FIG. 1 is a block diagram illustrating basic components of an automated system for storing, retrieving, and displaying medical images.

It is assumed, without further explanation, that axial and sagittal images obtained from an MRI apparatus will have been digitized and rendered into conventional scanned, pixelated data representations that can be processed by the computer system illustrated in FIG. 1. In FIG. 1, the system includes a DOS-based personal computer or work station 10 which has the capability to concurrently execute an application process 12 and a plurality of interface processes 14. The application process which, preferably, is written in the well-known C language, embodies processes and functions of the invention as described later in further detail. The interface processes 14 include commercially available programs as well as processes which can be constructed by the reasonably skilled computer programmer with the following description in hand. The interface processes 14 are connected to standard I/O devices such as a conventional trackball mechanism 16, a conventional QWERTY keyboard 22, and output devices 23 such as a full grey scale printer, a facsimile machine, and a modem (none of which is illustrated). The trackball mechanism 16 is a conventional picking device that includes a left button 18, a right button 19, and a rotation ball 20. The trackball mechanism 16 provides a user with the means for directly manipulating the position and functions of a cursor. The keyboard 22 is manually operated to input alphanumeric characters. The output devices 23 operate conventionally to provide tangible, visual results produced by the invention as described in further detail below. An image database 24 includes one or more conventional on-line storage devices for storage of medical image data representations which have been generated as described above. Therefore, the image database 24 includes not only the storage hardware, but also the stored images and all necessary indices. An output device 25 in the form of a multi-screen apparatus provides the means by which the images stored in the image database 24 are arranged and presented to a practitioner for examination, manipulation, and disposition. In the preferred embodiment, the device includes three separate output monitors 26, 27, and 28 which are connected by a coupling mechanism 29 to the interface processes 14 for control by the application process 12.

Figure 2:
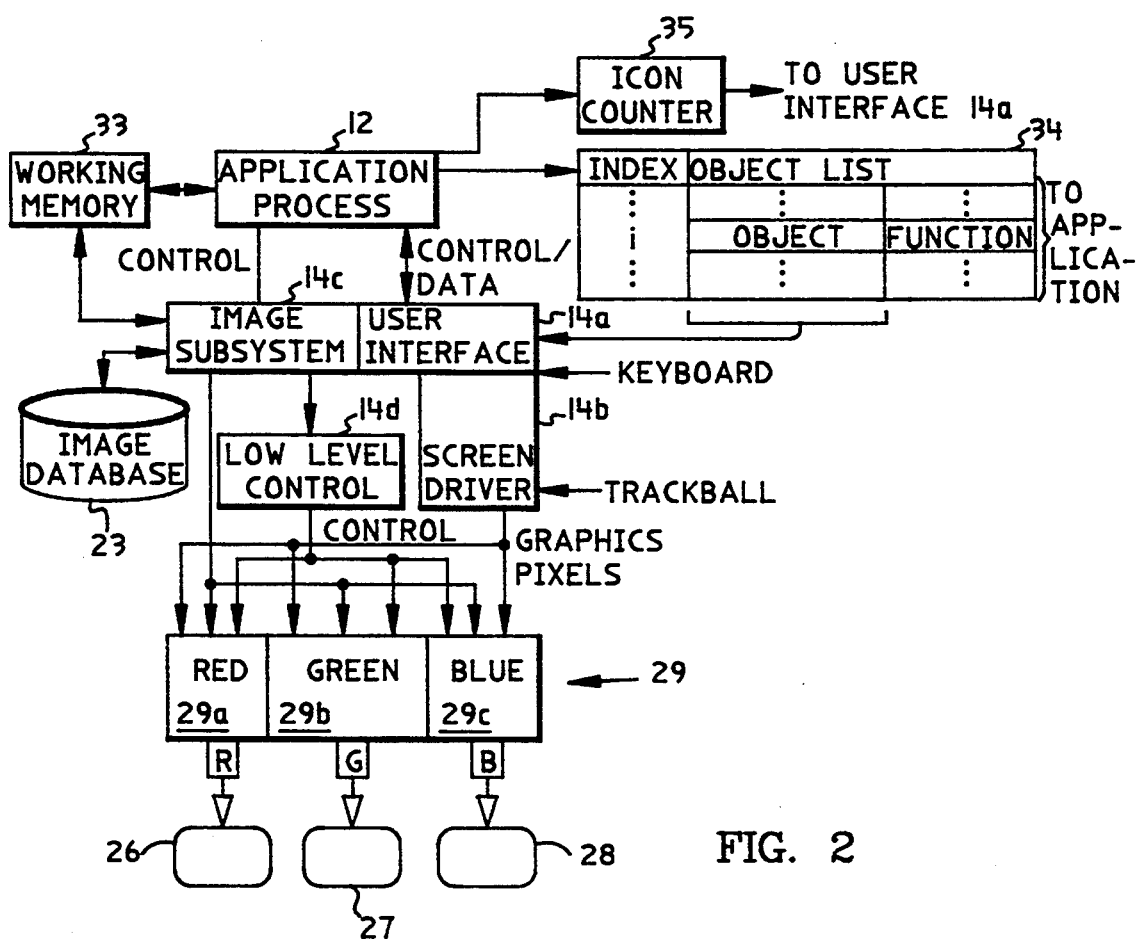
FIG. 2 is a block diagram illustrating in greater detail certain components of the system of FIG. 1.

FIG. 2 shows certain architectural aspects of the best mode for practicing the invention in a system such as that illustrated in FIG. 1. In FIG. 2, the interface processes 14 include a conventional directly-manipulated user interface 14a which is directly connected to a screen driver 14b. The screen driver 14b is connected to the trackball mechanism 16 and the keyboard 22, passing inputs from these devices by conventional means directly to the user interface 14a. The screen driver 14b also operates in conjunction with the user interface 14a to provide the pixel information necessary to draw and manipulate graphics on the monitors 26, 27, and 28.

The graphics include a cursor, display containers which give a visible structure for image presentation, and a control panel in which icons and function buttons are displayed. It is assumed that the user interface includes the ability not only to generate a cursor, but also to move the cursor among the monitors in response to trackball motion. It is further presumed that the user interface includes the ability to highlight icons and control buttons which have been "pointed to" by the cursor and "clicked" by a trackball mechanism button. The interface processes 14 further include an image subsystem 14c and a low level video controller 14d. The image subsystem 14c accesses the image database 23 for retrieval of stored images. Image selection is made by the application process 12 and indicated by control signals coupled to the image subsystem 14c. In response to control signals which designate images to be retrieved, the image subsystem 14c obtains the data representations of the specified images and enters them into a high-capacity working memory 33 as directed by the application process 12. The application process 12 further specifies how and which images in the working memory 33 are to be output on the monitors 26, 27, and 28. Thus, the pixel information representing database images flows from the working memory 33, through the image subsystem 14c to the monitors 26, 27, and 28. Control over the display apparatus 25 is provided by the coupling mechanism 29 in the form of a video card which has separately accessed and separately controlled memories for Red, Green, and Blue pixels. These memories are indicated by reference numerals 29a, 29b, and 29c, respectively. The memories of the video card are controlled by a low-level video controller 14d, which receives control signals from the image subsystem 14c. The image subsystem 14c generates control input for the low-level controller 14d in response to control signals generated by the application process 12.

In the architecture illustrated in FIG. 2, each of the memories 29a, 29b, and 29c is connected by a respective gun of a tri-color output to a particular video monitor. In particular, the Red memory 29a is connected by way of a Red (R) video output connector to the monitor 26, the Green memory 29b by a Green (G) video output connector to the monitor 27, and the Blue memory 29c by a Blue (B) video output connector to the monitor 28. The monitors 26, 27, and 28 are operated in the monochromatic mode and the memories 29a, 29b, and 29c are operated effectively as frame buffers for the monitors to which they are connected. This architecture merely reflects the design choices of the inventors in implementing the invention, and is not intended to limit the use of equivalent architectures. For example, instead of separate video monitors 26, 27, and 28, a designer might select an architecture which provides separate display containers (windows) on a single, large video monitor so that each window operates as a separate, independently-controlled monitor.

The application program 12 employs object-oriented programming techniques to provide programming controls and cues to the user interface 14a and the imaging subsystem 14c. Controls and cues are in an object list 34 which is initiated and updated as needed by the application process 12. The object list has a conventional structure in that it includes a plurality of objects, each of which represents some feature or attribute of a display which is presented on one of the monitors 26, 27, or 28. Objects in the object list 34 are conventionally indexed. Each object includes one or more application process functions and any data necessary to establish machine state when the object is encountered or otherwise identified during system operation.

The application process 12 maintains and increments an icon index 35 whose output is provided to the user interface 14a for accessing the object list 34 in a procedure described later in greater detail.

IMAGE PRESENTATION

The invention is practiced on a system architecture corresponding to that illustrated and discussed above. The invention is concerned with the presentation of one or more medical image series for consideration, analysis, and disposal by a user such as a radiologist. The invention includes at least two modes for presenting medical image series. The first mode is illustrated in FIG. 3.

Figure 3:
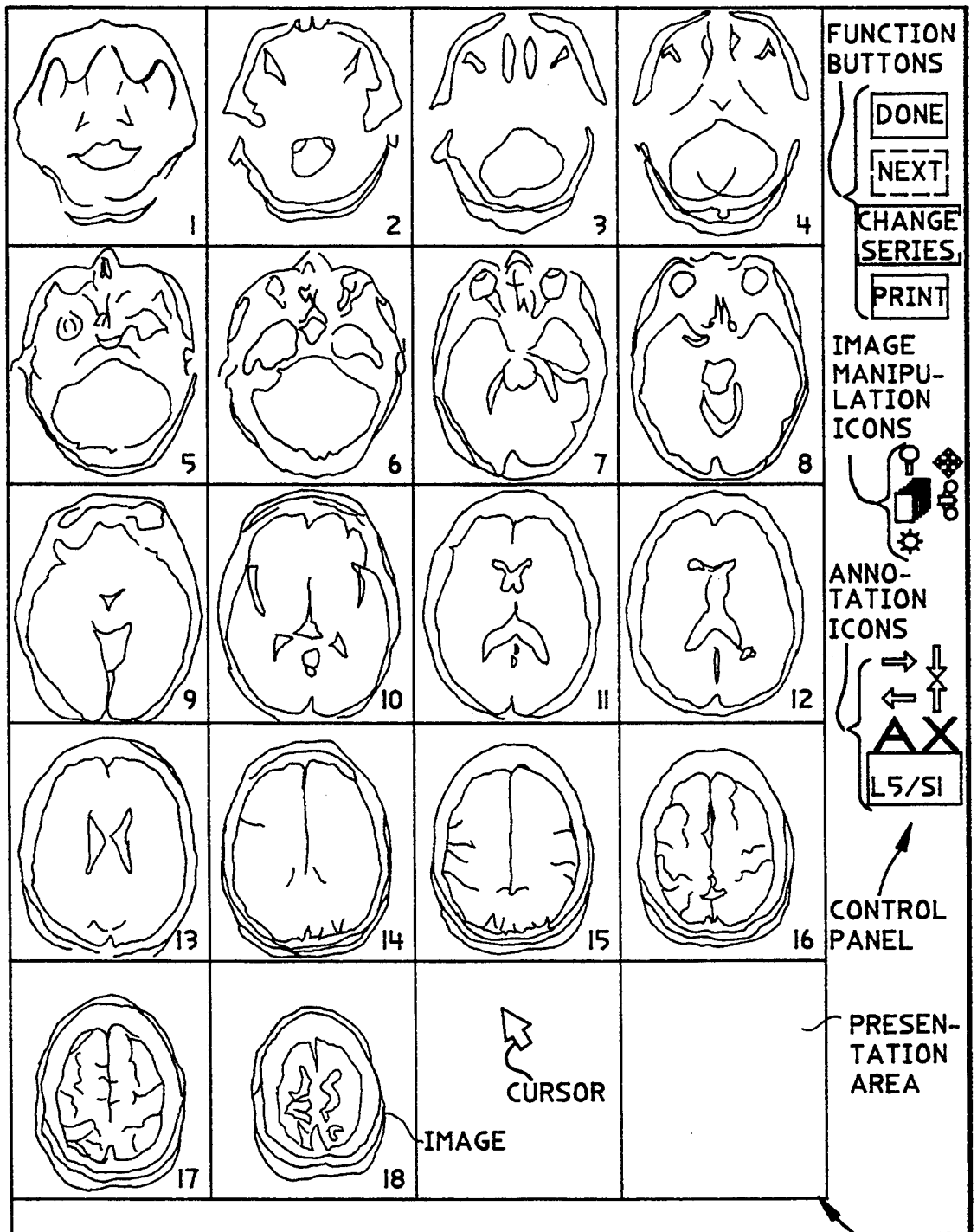
FIG. 3 is an illustration of a display container output on a monitor of the system of FIG. 1 for a presentation of medical images according to one mode of the invention.

FIG. 3 illustrates what is termed the "monitor" mode of image presentation. FIG. 3 illustrates a rectangular display container which is produced on one or more monitors for presentation of image series. The series shown in FIG. 3 is an axial T2 series including 18 images. The display container is subdivided into a rectangular array of 20 presentation areas. In the monitor mode of image presentation, an image series is shown in a single display container in its sequence order such that each presentation area of the display container includes one image of the sequence. Only one image series at a time is shown in any display container. Separate series are shown in separate display containers. The axial T2 sequence illustrated in FIG. 3 is ordered by assignment to each image in the series of a monotonically increasing number. The number assigned to an image represents the image's position in the sequence of which it is a member. In FIG. 3, therefore, the image in the upper left-hand presentation area is the first image of the axial T2 sequence, with the next image in the sequence being assigned the number 2 and being displayed in the next presentation area of the display container to the right of the presentation area where image number 1 is shown.

In the monitor mode of the presentation, a display container such as that illustrated in FIG. 3 is output on all but one of the monitors or monitor equivalents supported by the system. Thus, in FIGS. 1 and 2, a display container such as shown in FIG. 3 would be presented on, for example, monitors 26 and 27, with monitor 28 being reserved for presentation of a work product palette as described below. This permits more than one image series to be presented, with each image series being presented in its sequence order in a presentation area of a respective display container on a particular monitor. Since co-relative series such as axial T1 and axial T2 typically consist of an identical number of images taken at identical planes, identical side-by-side presentations of axial T1 and T2 series on adjacent monitors in the manner illustrated in FIG. 3 contributes significantly to a radiologist's ability to differentially analyze the images.

Figure 4:
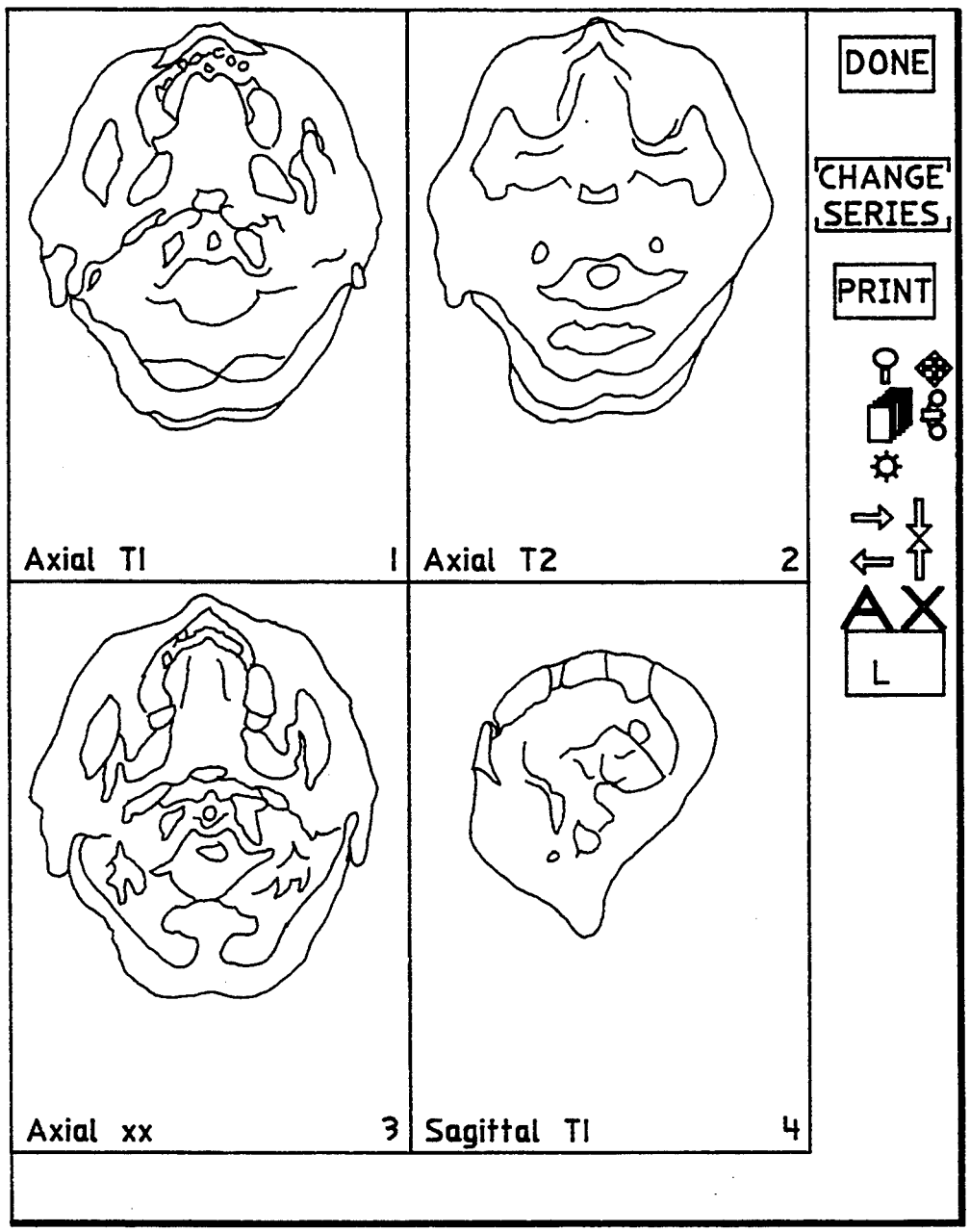
FIG. 4 is an illustration showing a display container for presentation of medical images according to a second mode of the invention.

FIG. 4 illustrates a second presentation mode of the invention which is termed the "series" mode. In the series mode, a display container comprising a rectangular array of rectangular presentation areas is displayed on one or more monitors. For example, the display container in FIG. 4 includes four substantially rectangular presentation areas numbered 1, 2, 3, and 4 in the drawing. In the invention, each presentation area of a series mode display container is employed to display an image series, one image at a time, in the order of its respective sequence. In this regard, consider presentation area 2 in which an axial T2 series is illustrated. Assume that the axial T2 series is identical to that illustrated in FIG. 3. Thus, the images of the axial T2 series would be shown in presentation area 2 beginning with image 1 and continuing sequentially until image 18 is shown. Assume next that a co-relative axial T1 series comprising 18 images is presented in presentation area 1 in the display container of FIG. 4. An important feature of the invention termed "coupling" is employed to synchronize the presentation of the axial T1 and T2 series so that whenever an image of one series is changed to the next image in the series, the other series is changed identically to display the image of the other series occupying the same sequence position. Thus, if presentation area 1 in the display container of FIG. 4 displays image 1 of the axial T1 series and then riffles through the images of the series, the display in presentation area 2 would identically riffle through the images of the axial T2 series, beginning with image 1. The invention contemplates that the coupling feature of the series mode of presentation will synchronize image presentation only between co-relative image series. Thus, for example, an axial T1 series would be coupled for a presentation with an axial T2 series, but not with a sagittal T1 series such as that shown in presentation area 4 of the display container in FIG. 4.

The series mode of presentation is practiced by presenting the display container of FIG. 4 on all available monitors or monitor equivalents except one, which is also reserved for the working palette display container.

Figure 5:
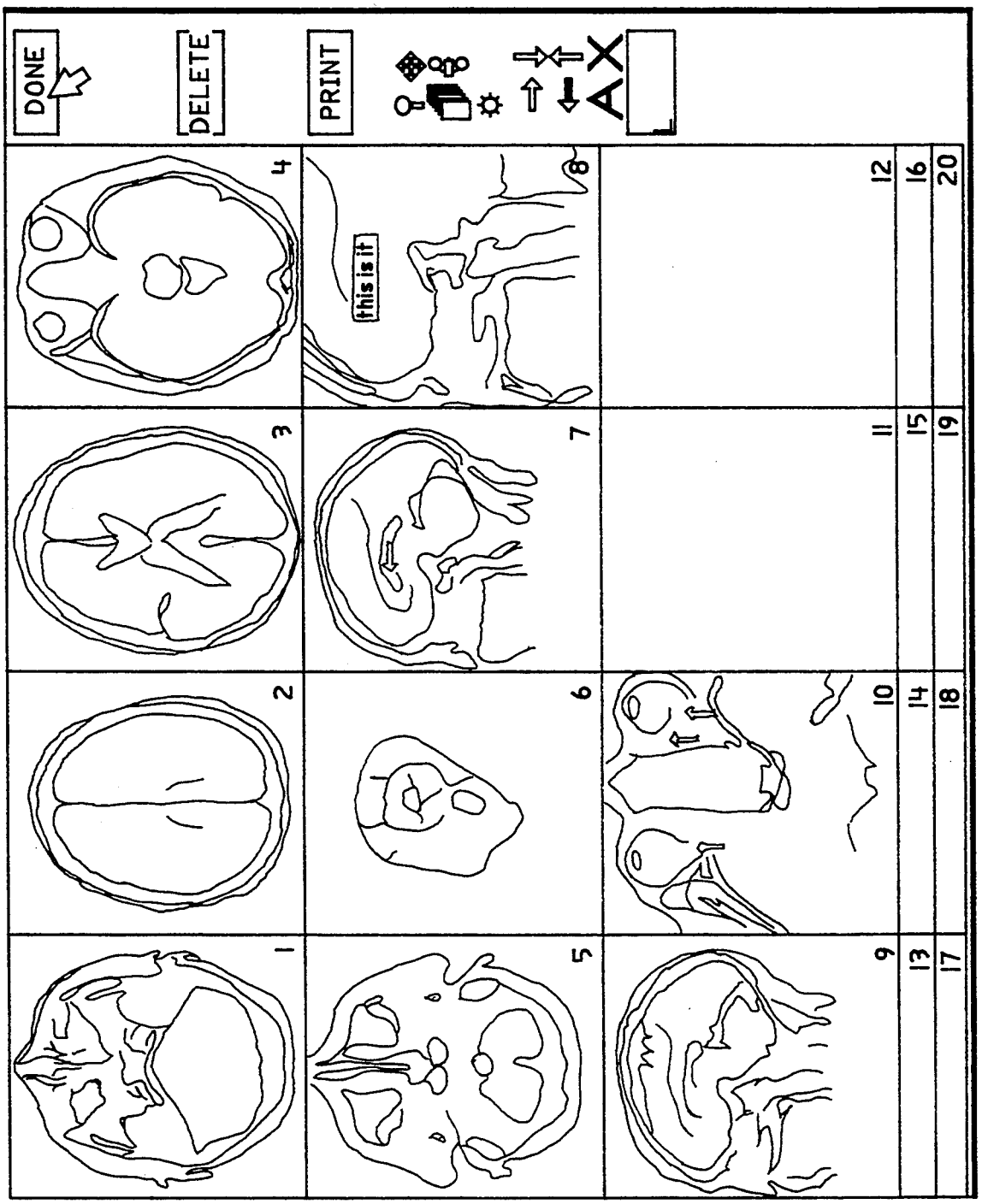
FIG. 5 is an illustration showing a working palette display container presented on a monitor of the system of FIG. 1.

Refer now to FIG. 5 for an illustration of the working palette display container. This display container is presented on one monitor of a multi-monitor system, such as monitor 28 in FIGS. 1 and 2. The working palette display container has a substantially rectangular aspect and is subdivided into a rectangular array of individual presentation areas. The working palette is provided to receive individual images which are picked and copied from presentation areas in monitor mode or series mode display containers. The working palette allows a radiologist to assemble the images which are deemed to be the most important in illustrating trauma or disease for provision to a referring physician. For example, the axial image displayed in presentation area 3 of the working palette display container may have been copied there from presentation area 12 in the monitor mode display container of FIG. 3.

Figure 6:
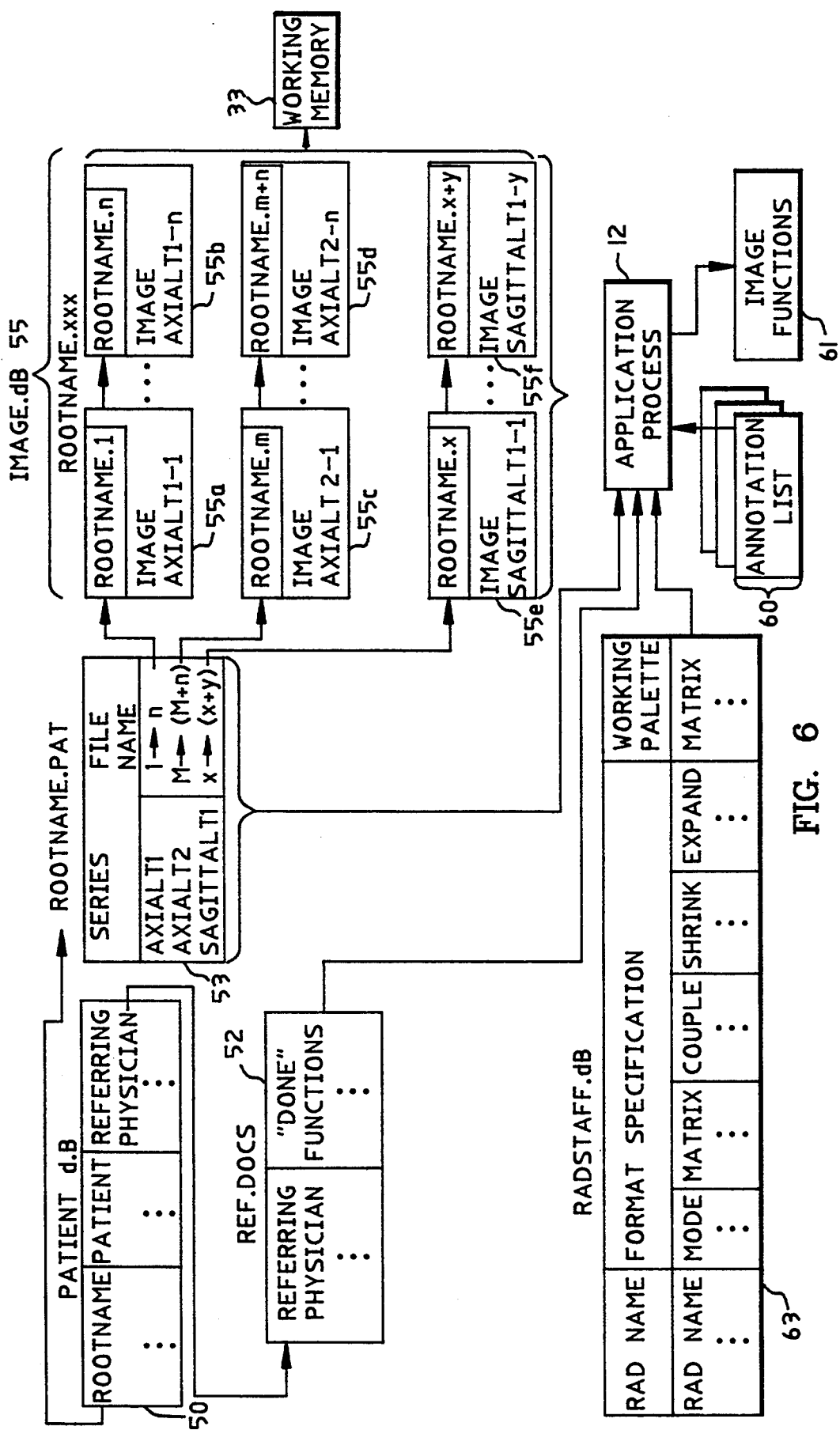
FIG. 6 illustrates the organization of a medical image database according to the invention.

FIG. 6 illustrates the structure of the image database which enables the efficient storage and retrieval of image series. When an MRI apparatus is used to generate images, examination protocols normally provide for identification of the patient, and set out the number and types of sequences which are to be taken and the anatomical target of interest. From this information, a unique composite patient identifier (ROOTNAME) is algorithmically derived. A patient, thus, has a unique ROOTNAME for each MRI examination. A patient identification, the corresponding ROOTNAME, and an identification of a referring physician are entered for each patient examination into a database file 50 entitled "PATIENT.dB". For any patient identification entered in the file 50, its corresponding ROOTNAME points to an examination file such as the file 53, which is entitled "ROOTNAME. PAT". Each examination file 53 identifies an image group including one or more image series obtained during an examination. Each image series in an image group is indexed to a set of sequentially named or numbered files in which the images of the series are contained. For example, in the ROOTNAME. PAT file 53 illustrated in FIG. 6, the image group includes axial T1, axial T2, and sagittal T1 series. The axial T1 series consists of n consecutively-numbered files, each containing a respective image of the series such that the sequence position of the named file corresponds to the sequence position of the image it contains. The image files are named ROOTNAME. XXX. Thus, image 1 in the axial T1 series has a file name ROOTNAME.1, the second image in this series is in a file named ROOTNAME.2, and so on. Similarly, the n images of the axial T2 series are stored in files consecutively numbered as ROOTNAME. m through ROOTNAME. (m+n). When a patient is identified to the application process 12, the application process determines a ROOTNAME value for that patient, obtains a ROOTNAME.PAT file, and commands the image subsystem to extract the image series contained in the ROOTNAME file sequence defined by the ROOTNAME.PAT file and place them in linked list form in the working memory 33. The application process 12 then presents the image series to a radiologist and provides the radiologist's work product assembled in a working palette, to the referring physician.

The file-naming rule for image series is important to the invention because it preserves the unique identity, and the order, of each image series. For any given ROOTNAME, an image series can be identified by reference to the ROOTNAME file 53 and manipulated, as a unit and independently of any other image series, by the system of FIGS. 1 and 2. This provides a very significant advantage over the existing systems which treat each image as an independent unit, unconnected with any other image in its sequence or with any other image in any other series or group.

As FIG. 6 illustrates, the PATIENT.dB file includes a REFERRING PHYSICIAN column containing values which index to entries in a REF.DOCS file 52. The REF.DOCS file 52 lists referring physicians. Each referring physician entry includes a set of functions specified by the identified referring physician which are to be executed when a radiologist indicates that examination of an image group is completed by pressing a DONE button, which is explained later in more detail. A RADSTAFF.dB file 63 includes at least seven columns. In the first column (RAD NAME) are listed the names of radiologists having access to the system. The second through sixth columns comprise a format specification for the monitors in which the image series are to be displayed. The seventh column includes a working palette specification. The format specification, columns two through six of the Table 63, include a MODE column, identifying the monitor or series mode of presentation, a MATRIX column setting forth the number of rows and columns in the display containers, and a COUPLE column specifying whether the coupling function is invoked for synchronization of two or more image series in a series mode of presentation. The format specification further includes SHRINK and EXPAND columns which specify whether the rows and columns of the matrix are to be adapted to predefined dimensional parameters for display containers. The seventh column specifies the matrix size of the working palette. The application process also has access to a set of annotation lists 60 and to the set of image functions that are linked to objects which are in or which may be added to, the object list 34 of FIG. 2.

Figure 7:
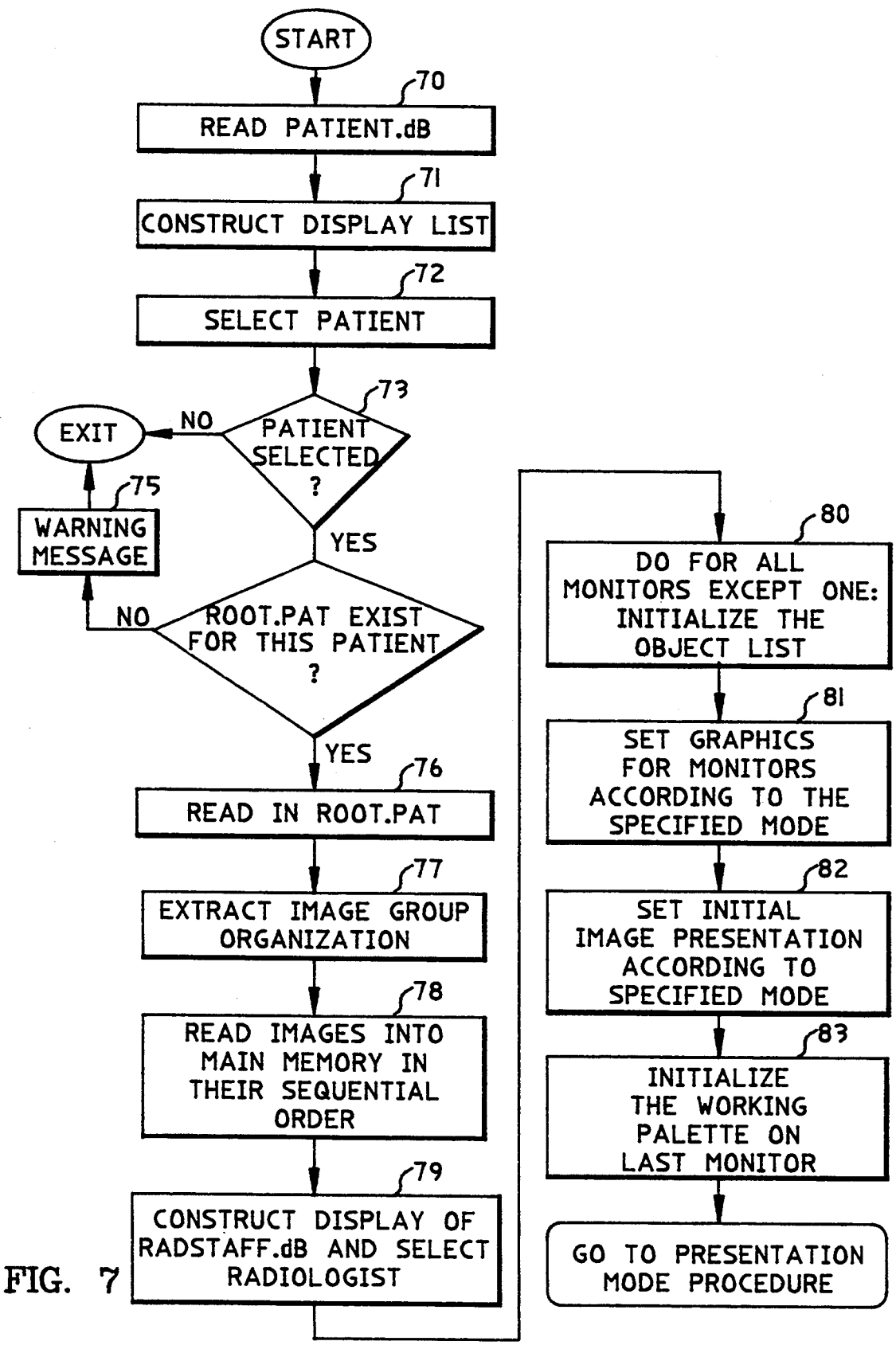
FIG. 7 is a flow diagram illustrating how the database of FIG. 6 is accessed.

FIG. 7 illustrates the procedure executed by the application process 12 to initialize the system of FIGS. 1 and 2 for presentation of images. The procedure starts at step 70 by receipt of an indication that the PATIENT.dB file is to be read. In step 71, a list illustrating the PATIENT.dB file is constructed and presented on one of the monitors. It is assumed that the user can select the name of a patient simply by moving a cursor to the patient's name in the displayed list and clicking on the name by depressing and releasing a trackball button. The decision 73 awaits selection of a patient. In decision 73, the negative exit can be manually selected. If the negative exit is taken from decision 73, the procedure is exited. If a patient is selected, the positive exit is taken from decision 73 and a search is conducted of the database for a ROOTNAME.PAT file for this patient in step 74. If the file does not exist, a warning message to the operator is displayed on the monitor in step 75. Otherwise, the ROOTNAME.PAT file is provided to the application process which extracts the image group organization from the file in step 77, and passes the appropriate control signals to the imaging system in step 78 to enable the imaging subsystem to copy the images named in the ROOTNAME.PAT file from the image database to the main memory. In step 79, a list illustrating the RADSTAFF.dB file is presented in a manner permitting a radiologist to log on by pointing to and clicking his name in the list. When the radiologist's name is identified in this manner, the format specification and working palette matrix size in the same RADSTAFF.dB row are provided to the application process 12 which enables it to initialize control blocks for each monitor, as well as the object list, in step 80. The object list includes a full specification of the graphics objects required in the first monitor for the mode and the matrix size, and palette size specified in the RADSTAFF.dB entry selected by the user. The first monitor is then initialized with graphics and images in steps 81 and 82. Once the first monitor has been initialized, the object list is updated for specifying tile graphics of the second monitor, and then is updated once again to specify the working palette graphics for the third monitor. The third monitor is initialized with graphics in step 83. The application process then executes the appropriate presentation mode procedure. In the preferred embodiment, the monitors 26 and 27 in FIGS. 1 and 2 are formatted with display containers of the specified mode and matrix size and populated with images and then the monitor 28 is formatted with the specified working palette.

Referring once again to FIGS. 1 and 2, when the object list 34 is initialized or updated, the application process provides a "SELECT MONITOR" control signal to the image subsystem 14c. This signal is appropriately conditioned to indicate the monitor to which control is to be transferred. In response, the image subsystem configures the low level controller 14d to enable the appropriate one of the memories 29a, 29b, or 29c. For example, when the object list is initialized, the SELECT MONITOR control signal forces the low level controller 14d to enable the Red memory 29a to receive the appropriate display container graphics established in the object list 34. The user interface 14a inspects the object list 34 to determine the graphics objects for which graphics pixels must be generated and provided by the screen driver 14b. The screen driver 14b outputs the specified graphics pixels in parallel to all of the memories 29a, 29b, and 29c. The pixels, however, are read into only the currently-enabled memory.

Once the series of an image group have been entered in sequence order into the working memory 33 and the display containers have been initialized, the application process produces the appropriate image system control signals to present an initial image display in the specified presentation mode. If, for example, the monitor mode has been specified, graphics pixels for presenting a display container such as that illustrated in FIG. 3 in the specified matrix size are entered into the Red memory 29a of the video card together with image pixels for the first series of the image group. When the memory 29a is appropriated loaded with graphics and image pixels, the application process issues a SELECT MONITOR control signal to the low level controller 14d through the image subsystem 14c, which disables data entry to the Red and Blue memories 29a and 29c and enables data entry into the Green memory 29b. Graphics pixels and image pixels for the second series of the image group are entered into the memory 29b and the SELECT MONITOR signal is once again issued so that graphics pixels for the working palette can be entered into the Blue memory 29c. Next, the object list is updated to describe the Red memory 29a, the Red memory 29a is enabled, and the cursor is generated. The cursor pixels are fed to the enabled memory and updated therein when the cursor is moved.

At this point, display containers with images would be presented on the monitor 26 and on the monitor 27, while an empty working palette would be displayed on the monitor 28.

Returning to FIG. 3, assume that the monitor display container and image series in this figure are displayed on monitor 26 as shown in the figure. Thus, the presented display includes a rectangular area adjacent the right edge of the display container. This area is referred to as the "control panel" and contains a plurality of function buttons (DONE, CHANGE SERIES, and PRINT), a set of image manipulation icons immediately below the function buttons, and a set of annotation icons below the image manipulation icons. Any of the function buttons and any of the image manipulation or annotation icons can be activated by "point and click" using the trackball to point with the cursor, and the left cursor button to click on a button or icon.

The function buttons represent application process functions that can be activated by pointing and clicking. The DONE button, when activated, invokes the "DONE" functions of the referring physician. The CHANGE SERIES button, when activated, deletes the series presently displayed in the display container and enters the images of the next series listed in the ROOTNAME.PAT file. The PRINT button invokes an application process function which prints a copy of the screen. As also illustrated in dashed outline in FIG. 3, another button may be presented in a control panel between the DONE and CHANGE SERIES buttons. The button may be a NEXT or a PREVIOUS button. When the image series includes more images than there are presentation areas in the display container, the NEXT button replaces the currently-displayed subset of consecutively numbered images of the series with the following subset. So long there are images remaining to be presented, the NEXT button will be presented. When the last subset of the image series is displayed in the display container, the PREVIOUS button is displayed. When activated, the PREVIOUS button returns the previous subset of series images in the display container. It should be evident that the NEXT and PREVIOUS buttons are displayed only in monitor mode control panels.

The set of image manipulation function icons is positioned immediately beneath the PRINT button. These icons control various image manipulation functions. The upper left-most icon is a magnifying glass and controls a conventional zoom function which magnifies or minifies an image in response to trackball motion. Immediately beneath the zoom icon is a riffle icon in the form of a spaced set of pages. In response to trackball motion, the riffle function shuffles through an image series in forward or reverse sequence. Beneath the riffle icon is an icon representing illumination which adjusts the contrast or brightness of an image in response to trackball motion. Immediately to the right of the zoom icon is a roam icon consisting of four outwardly-directed arrows. The roam function is used in conjunction with the zoom function and moves a magnified image under a viewing aperture in response to trackball motion. The icon in the shape of a movie camera immediately beneath the roam icon denotes the cine function, which is an automated riffle that, once selected, automatically steps through an image series in sequence order. The speed of the cine function is controlled by the trackball.

A set of annotation icons consisting of four arrows and A and X and a rectangular box is presented immediately beneath the image manipulation icons. These icons are discussed later in more detail.

As FIGS. 3 and 4 illustrate, the cursor has a default shape in the form of a hollow arrow.

Figure 8:
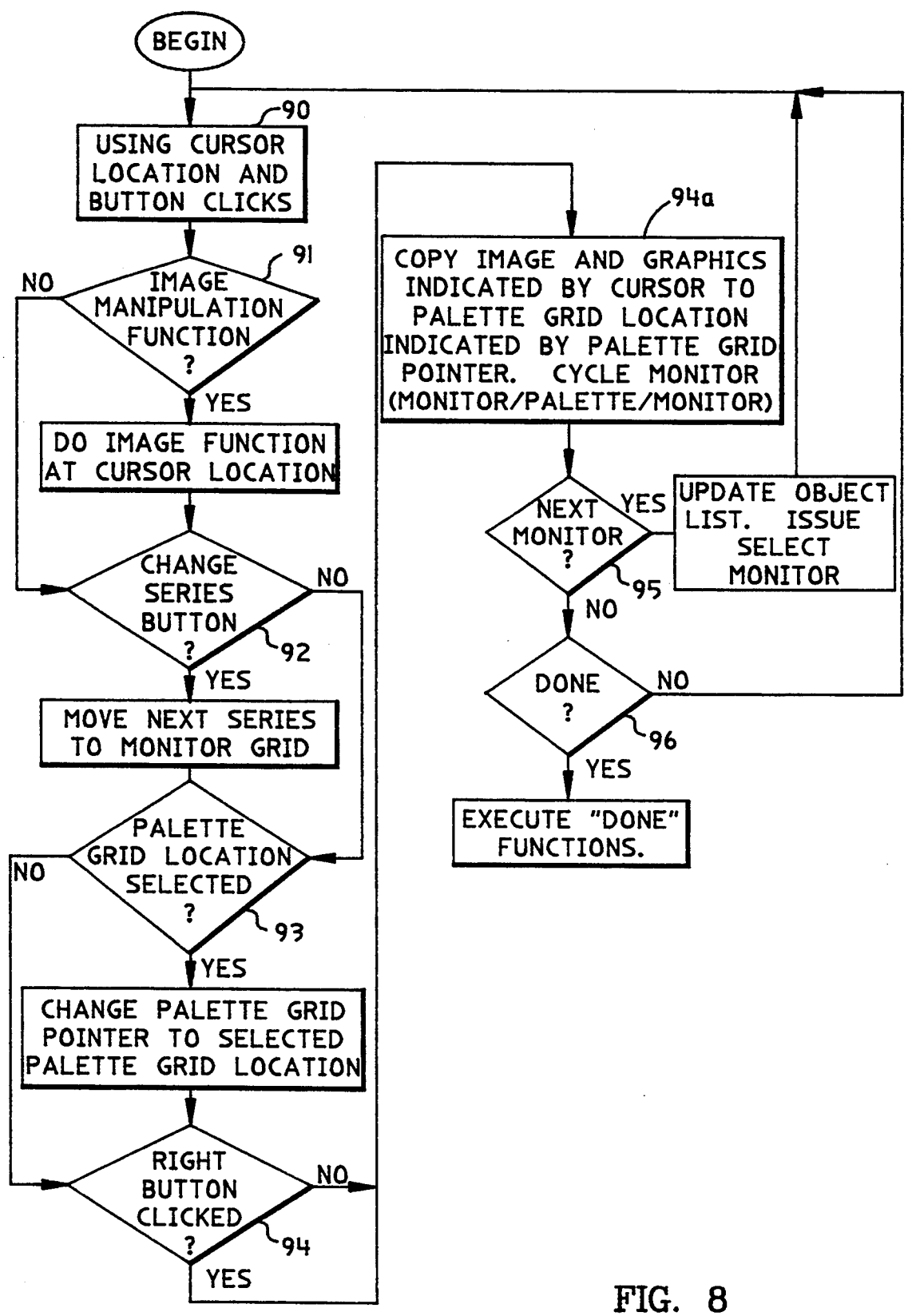
FIG. 8 is a flow diagram illustrating how the system of FIGS. 1 and 2 presents images according to the first mode of the invention.
Figure 9:
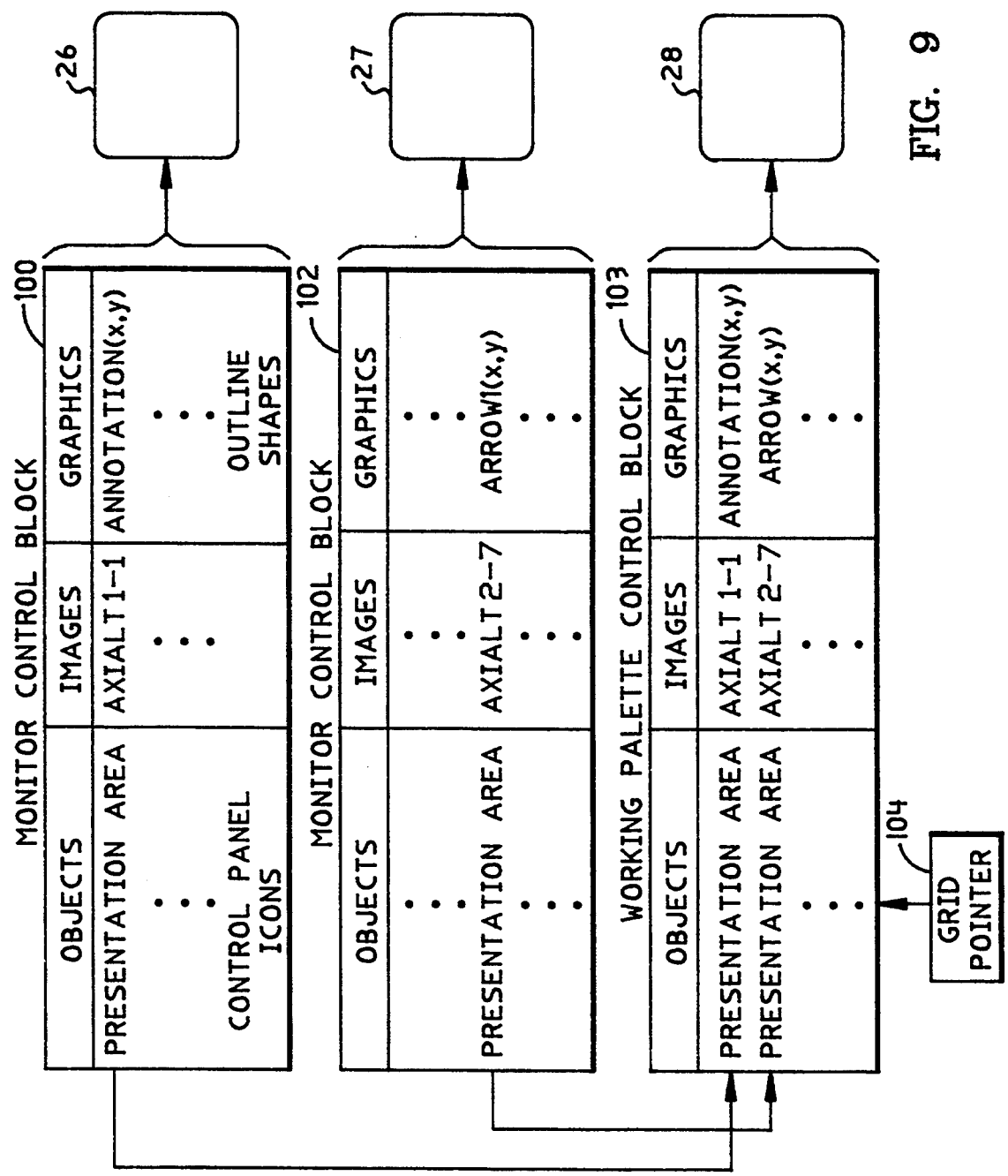
FIG. 9 is a block diagram illustrating presentation of images according to the first mode of the invention.

Refer now to FIGS. 3, 8, and 9 for an understanding of a monitor presentation format procedure according to the invention. Once the displays in the monitors 26, 27, and 28 have been initialized for monitor presentation as described above, the monitor format procedure begins. This procedure executes in response to cursor location and trackball button activation. Thus, in step 90, beginning with monitor 26, for example, and using the cursor location and sensing button activation, the procedure determines whether one of the image manipulation icons has been selected in decision 91. If so, the image function is performed at the cursor location. Otherwise, the negative exit is taken from decision 91 and the status of the CHANGE SERIES button is inspected in decision 92. If the button function has been activated, the next series listed in the ROOTNAME.PAT file is moved into the display container grid of the monitor where the cursor is located when the left button of the trackball mechanism is clicked. Now, a series counter (not shown) for the monitor is updated to identify the series currently displayed on the monitor. If the function has not been activated, the negative exit is taken from decision 92. In decision 93, the application process determines whether a working palette grid location has been selected for placement of an image. In this regard, the application process maintains a working palette grid pointer which is updated to the next working palette grid location when an image is moved to the current one. The grid pointer can also be forced to a grid location by moving the cursor from the monitor where it is currently located to the monitor where the working palette is displayed and pointing and clicking a grid location in the working palette display container. Preferably, a working palette grid location is selected by clicking the left button of the trackball mechanism. (Once an image has been moved to a preselected working palette grid location, the grid pointer is reset to indicate the next empty grid location which was available before user selection.) The cursor is then returned to a monitor which shows an image series. Decision 94 assumes that the cursor is in a presentation area of the monitor mode display container. If the right button of the trackball mechanism is clicked, the application process infers that the user wants the image in the presentation area moved to the working palette grid location indicated by the palette grid pointer. In this case, the image at the cursor location and any annotation graphics which it contains are copied in step 94a into the working palette grid at the location indicated by the working palette grid pointer. Refer to FIG. 9 for an understanding of how the application process accomplishes this step.

In FIG. 9, three monitor control blocks 100, 102, and 103 are illustrated. The application process maintains the control blocks, each of which completely describes in object form the current display on a particular monitor. For example, the monitor control block 100 lists the identification and location of each graphical object displayed on the monitor 26. This would include a complete object description of a monitor mode display container, a control panel, if a monitor is active, and the images of the series presented in the display container. For example, consider the first image of an axial T1 series which is listed in grid location 1, corresponding to the upper left-hand presentation area in the display container of FIG. 3. The monitor control block 100 also lists the graphics displayed at the grid location. When an image is to be moved to the working palette it is copied from the object indexed by the current cursor location in the control block of the monitor where the cursor is located to the palette monitor control block at the grid location indicated by the working palette grid pointer 104. In order to effect the update on the working palette display container presented on the palette monitor 28, the application process, using the palette monitor control block, updates the object list to describe the updated working palette display container and issues a SELECT MONITOR control signal. In response to the SELECT MONITOR control signal, the image subsystem accesses the working memory to obtain the pixels for the image to be moved and enters them into the Blue memory 29c which has been enabled by the SELECT MONITOR signal. At the same time, the screen driver 14b provides any annotation pixels for the image which may be described in the object list. This causes the selected image and accompanying graphics to be added to the working palette presented on the monitor 28. When entry of the image and graphics pixels in the Blue memory 29c is complete, the application process updates the object list to describe the display presented in the monitor where the cursor is located and issues a SELECT MONITOR signal to enable the corresponding color memory.

In decision 95, the application process inspects the cursor location to determine whether the cursor has been moved to another monitor. If so, the object list is updated to the configuration of the monitor where the cursor is located and the SELECT MONITOR control signal is conditioned to enable the corresponding color memory for the new monitor.

In decision 96, if a DONE button is selected, the application program executes the DONE functions for the referring physician. These may include, for example, simply printing out a hard copy of the working palette display container and entering the printout into the patient's file, faxing a data or an image copy of the working palette display container to a predetermined location, or transmitting a data representation of the working palette monitor through a modem to a predetermined location.

Figure 10:
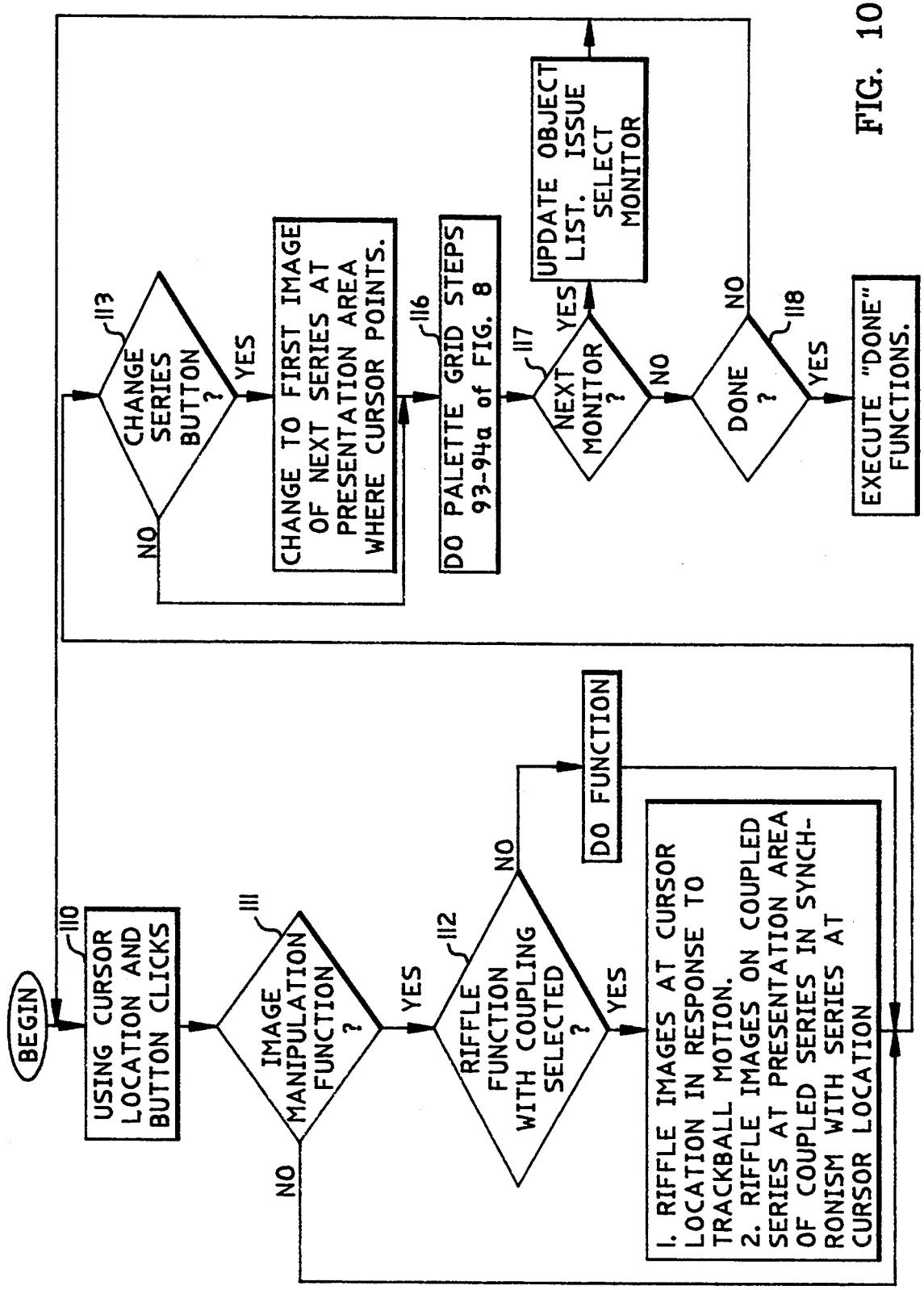
FIG. 10 is a flow diagram illustrating how the system of FIGS. 1 and 2 presents images according to the second mode of the invention.
Figure 11:
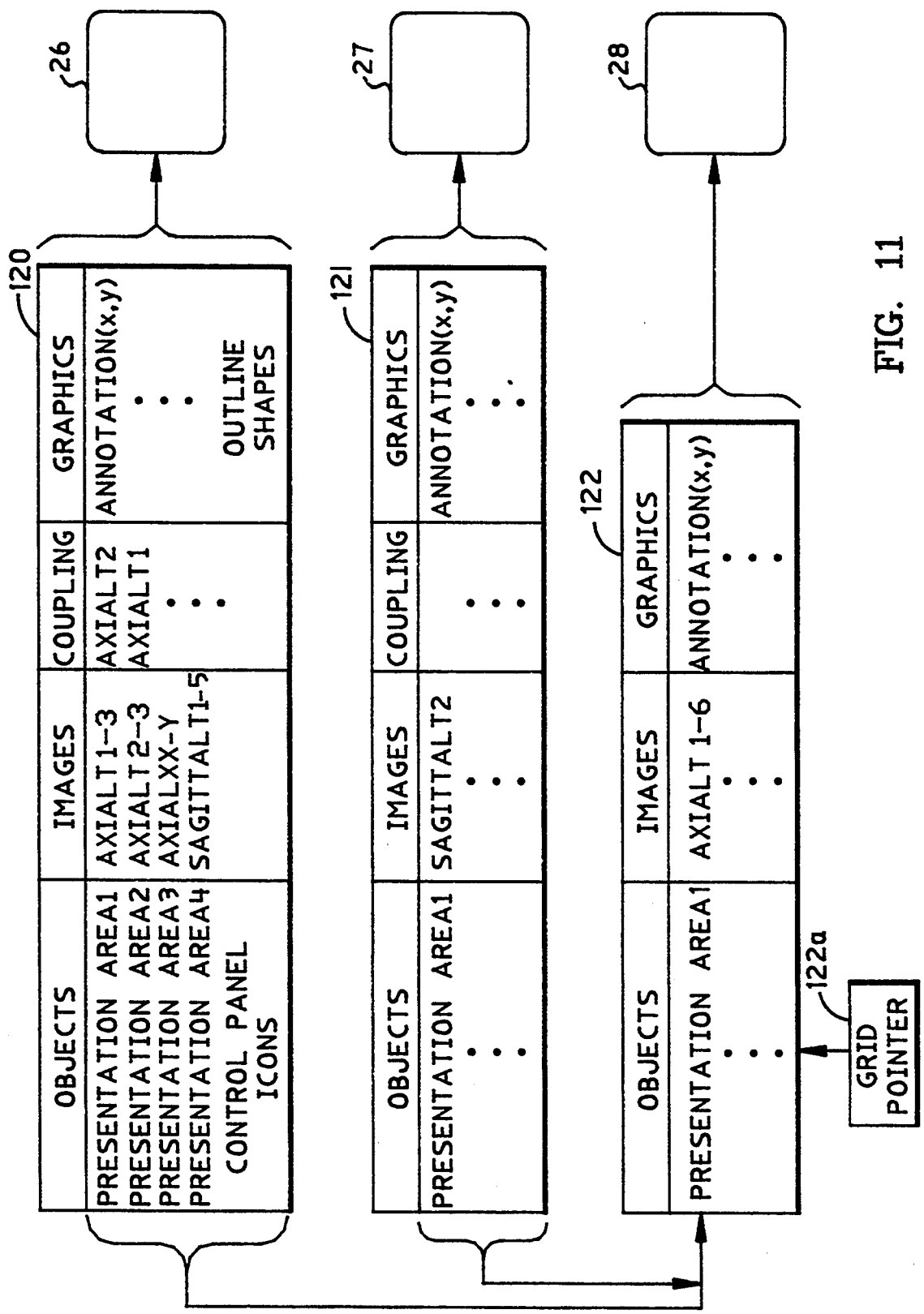
FIG. 11 is a block diagram illustrating presentation of images in a database of FIG. 6 according to the second mode of the invention.

Refer now to FIGS. 4, 10, and 11 for an understanding of a series presentation format procedure according to the invention. Once the displays in the monitors 26, 27, and 28 have been initialized for series presentation as described above, the format procedure begins. This procedure executes in response to cursor location and trackball activation. Thus, in step 110, beginning with monitor 26, for example, using cursor location and sensing button activation, the procedure determines whether one of the image manipulation icons has been selected in decision 111. If so, the image manipulation function is filtered at decision 112 to determine whether the riffling function has been invoked with the coupling feature selected. If not, the negative exit is taken from decision 112 and the image manipulation function is performed in the presentation area where the cursor is located. On the other hand, if the riffling function has been invoked with coupling activated, the positive exit is taken from decision 112. Here, the images of the series being output through the presentation are where the cursor is located are riffled (in response to trackball motion) in the presentation area where the cursor is located. In addition, the images of any coupled series are riffled at the presentation area where the coupled series is displayed. The riffling is in synchronism with riffling the series at the cursor location. Decision 113 tests the CHANGE SERIES button of the control panel. If the button has been activated, the procedure waits until the cursor is moved to a display container presentation area and the left button is clicked. Then, the series is changed to the next ROOTNAME.PAT file image series. When the series is changed, the first image of the next series is displayed at the presentation area where the cursor is located. Step 116 moves images to the working palette display container in the manner described above for the monitor presentation format. Next, monitor processing and DONE button processing are performed in decisions 117 and 118 as discussed above in connection with FIG. 8.

FIGS. 4 and 11 illustrate how the working palette is populated with images during the series presentation mode. In the series presentation mode, the application process maintains a monitor control block for each of the monitors 26, 27, and 28. The monitor control blocks are, respectively, 120, 121, and 122. Assume that the series presentation display containers such as the display container illustrated in FIG. 4 are presented on the monitors 26 and 27. For each monitor, the control block must list the principal objects which, for the display container of FIG. 4, are the four presentation areas of the control panel and the icon control panel. The control block links a respective series with each of the presentation areas in the IMAGES column of the block. In the COUPLING column, a related image series is listed if the coupling function has been invoked. The GRAPHICS column lists the graphics for, and in, each presentation area. The monitor control block 121 fully describes the display container and control panel displayed on the monitor 27, while the control block 122 fully describes the working palette presented on the monitor 28. A grid pointer 122a is used to denote the current working palette grid location in the manner described above in connection with FIG. 9.

ACTIVE MONITOR INDICATION

The invention also includes the ability to indicate, by the control panel, which monitor is currently active. In this regard, the "active" monitor is most likely the one wherein the cursor is currently located. The configuration of the active monitor is fully described in the object list; user inputs are received through it; and application response is provided through it. Manifestly, it would be inefficient and distracting to the user to have to remember which monitor is active by devoting full attention to the cursor's location. Positioning the cursor in a particular monitor might, in some instances, not indicate the active monitor. In addition, as described later, the shape of the cursor may change, causing the user to lose track of it and the active monitor.

In the invention, the active monitor is indicated by the presence of a control panel. Preferably, when a user moves a cursor to a monitor boundary which is shared with another monitor, the cursor is moved from the one monitor (which is called the "last" monitor) to the monitor which is adjacent the boundary of the last monitor (which is called the "next" monitor). The last monitor is then deactivated and the next monitor is activated. In response to movement of the cursor from the last monitor to the next, the control panel in the last monitor is turned off and the control panel is presented in the next monitor.

Figure 12:
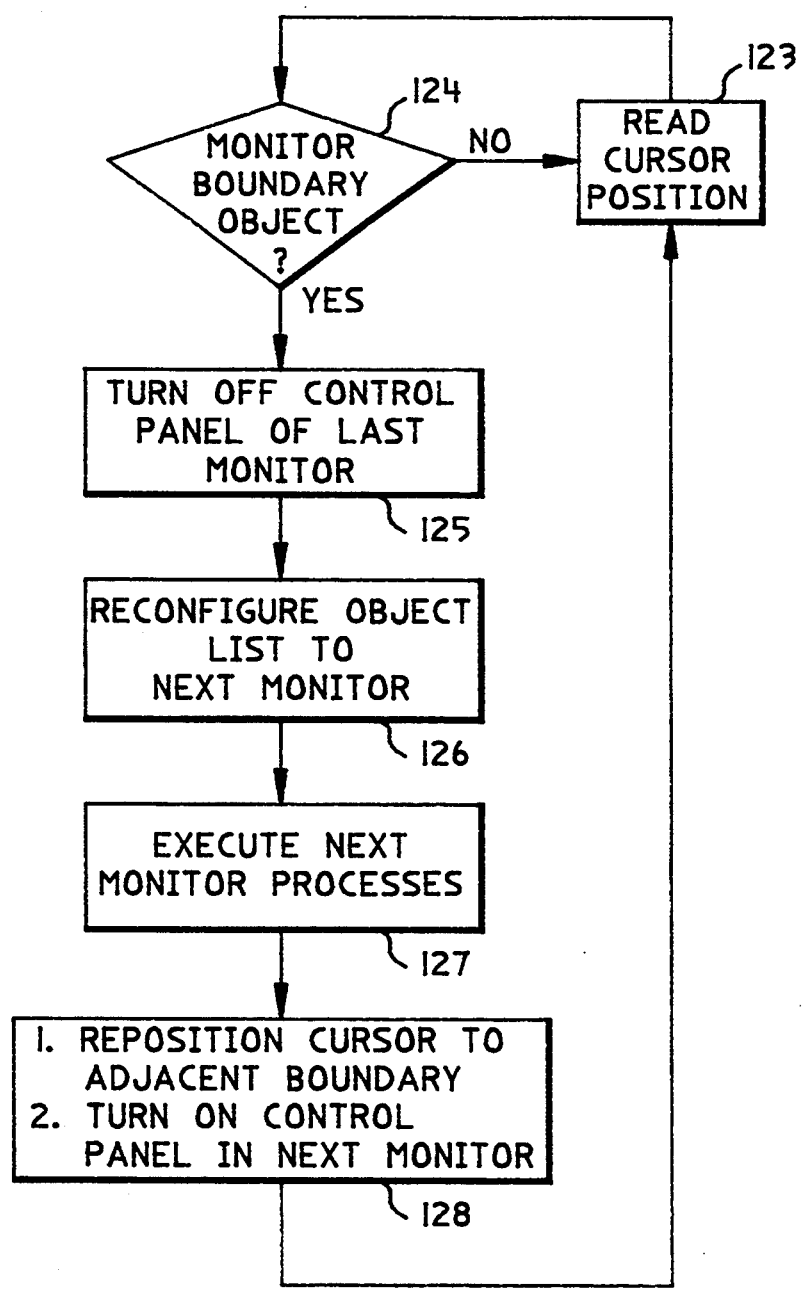
FIG. 12 is a flow diagram illustrating a procedure for indicating an active monitor according to the invention.
Figure 13:
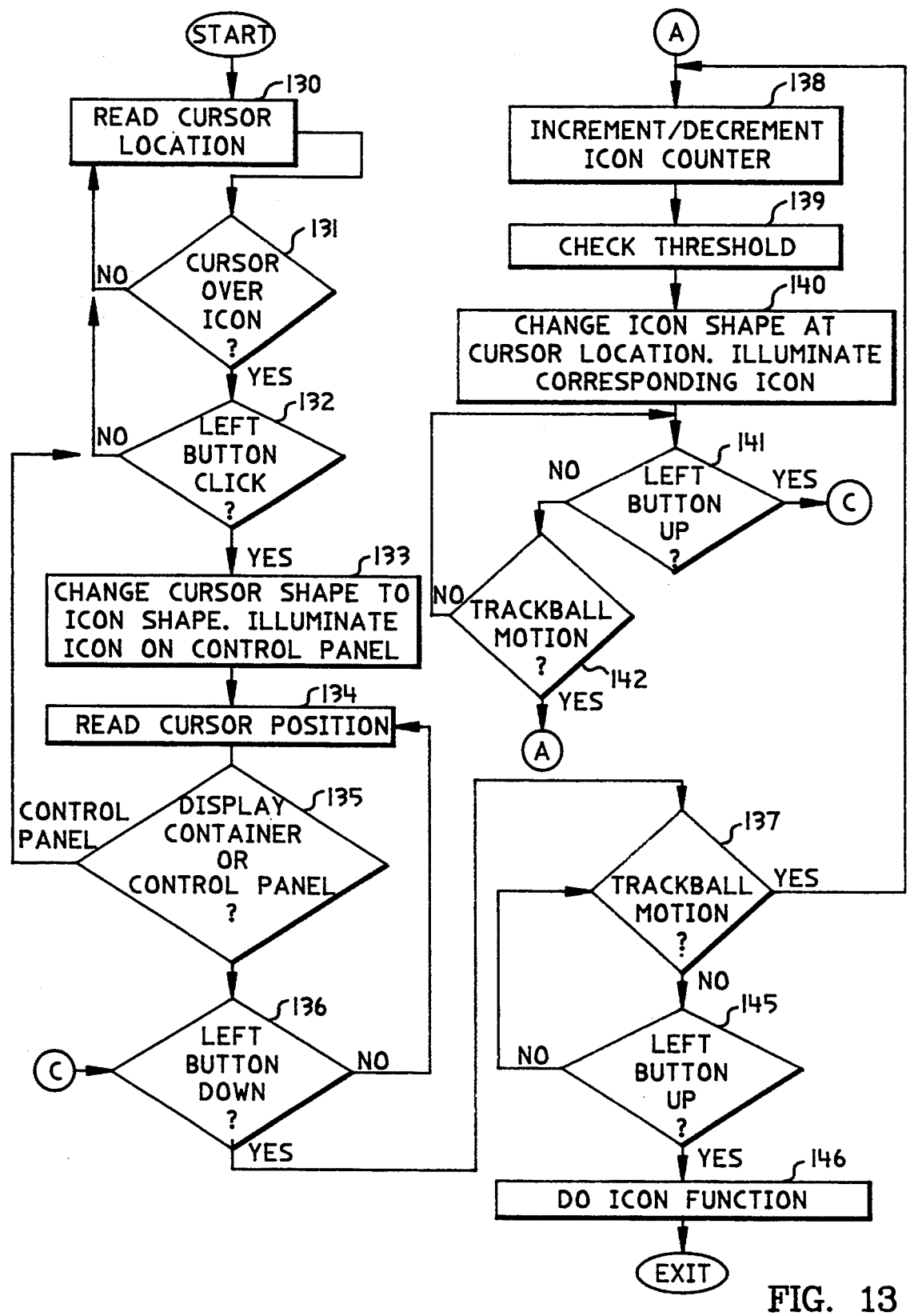
FIG. 13 is a flow diagram illustrating a procedure for rotating image manipulation icons according to the invention.

The procedure for performing the active monitor indication function is illustrated in the flow diagram of FIG. 12. Initially, the cursor position is read in step 123. When the cursor location is the same as the location of a boundary object defined in the object list of the current monitor, the application process prepares to deactivate the present monitor. In this regard, the positive exit is taken from the decision 124 and the application process issues control signals which turn off the control panel of the last monitor in step 125, reconfigures the object list to define all of the objects, including the boundaries, in the next monitor in step 126, and then executes a series of next monitor routines in step 127. One next monitor routine is conditioning of the SWITCH MONITOR signal to enable the color memory for the next monitor. Additional next monitor routines are shown in step 128. In step 128, cursor graphics pixels are configured to place the cursor adjacent the boundary in the next monitor which is closest to the last monitor. Next, the control panel is turned on in the next monitor and the procedure returns to step 123.

The control panel deactivation/activation sequence to indicate monitor activation is not necessarily limited to turning off the control panel in the last monitor and turning on the control panel in the next monitor. Other visual cues may be used. For example, the control panel colors may be inverted or changed in intensity.

ICON ROTATION

The invention also provides a "heads up" feature which permits a user to select an image manipulation icon without shifting attention from a presentation area to the control panel. This is accomplished by moving the cursor one time to an image manipulation icon in the control panel, changing the shape of the cursor to that icon, moving the cursor back to a presentation area, and rotating the shape of the cursor at that location through the succession of image manipulation icon shapes in response to motion of the trackball, and selecting an icon function at the location where the cursor shape has been changed.

Figure 14A:
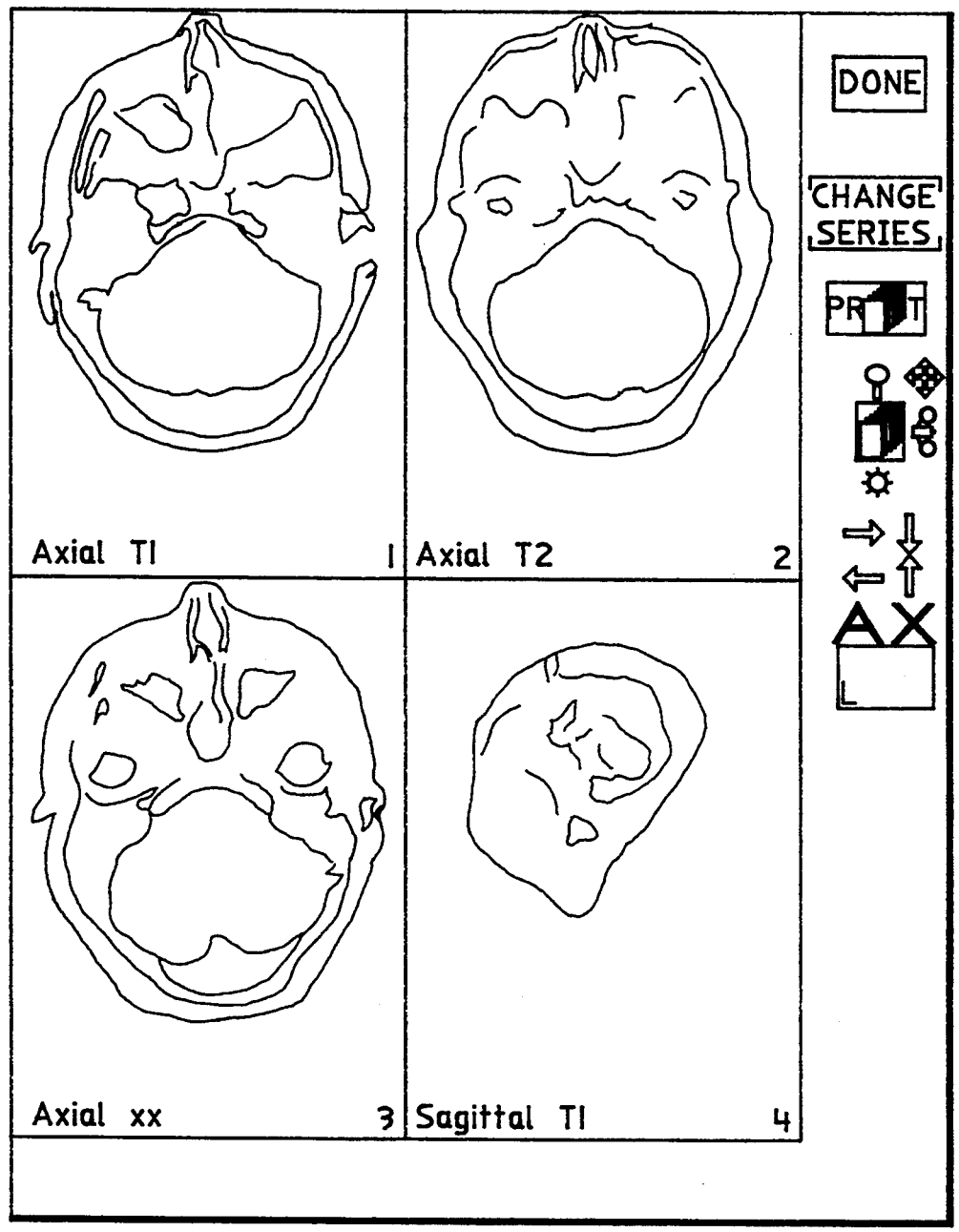
FIGS. 14a through 14d are illustrations of display containers showing icon rotation according to the procedure of FIG. 13.
Figure 14B:
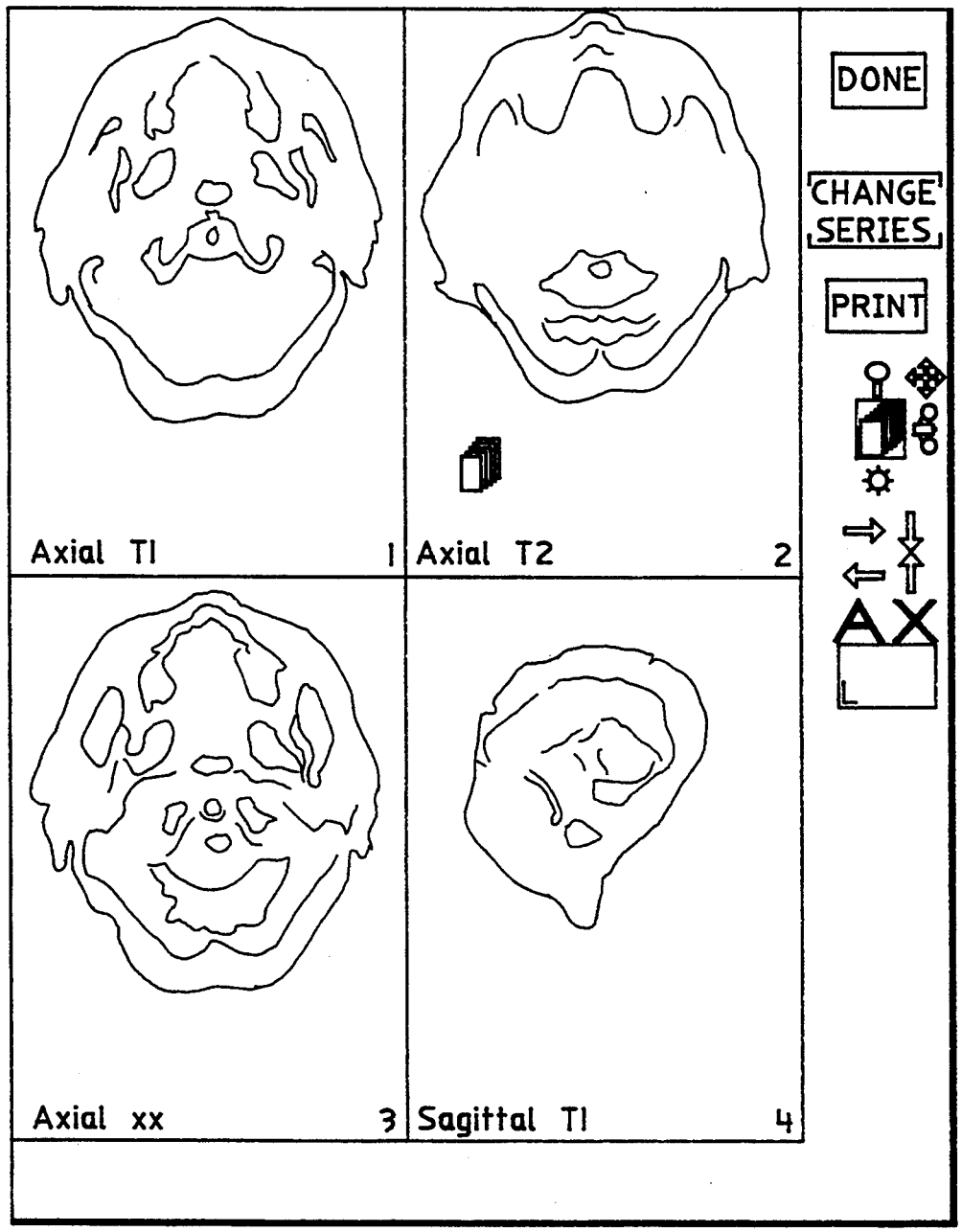

Refer to FIGS. 13 and 14a–14d for an understanding of the icon rotation function of the invention. Initially, in decision 131, the cursor position read at step 130 is evaluated to determine whether it is over one of the image manipulation icons in the control panel. Positioning the cursor over one of these icons and clicking the left button causes the cursor to change its shape from a default shape (preferably, a hollow arrow) to the shape of the selected icon and results in illumination of the icon at the control panel as provided in step 133. The result of performing step 133 is illustrated in FIG. 14a where the shape of the cursor has been changed to the riffle icon shape comprising a set of pages. Selection of the icon at its control panel location will not immediately invoke the corresponding function because the image manipulation functions are intended to execute with respect to a selected image. Thus, to invoke the selected function, the cursor, now in the shape of the selected icon, must be moved to one of the presentation areas. Therefore, in step 134, the position of the cursor (now in the shape of an icon) is read and when decision 135 determines that the cursor is in an image display container, the positive exit is taken and decision 136 checks the status of the left button on the trackball mechanism. If the left button is not down, the procedure loops through 134, 135, and 136 until it detects depression of the left button. When the left button is held down and the trackball is moved, the shape of the cursor is successively changed to the shapes of the image manipulation icons in their order of presentation in the control panel. This is illustrated in FIG. 14b where the cursor, in the shape of the riffle icon, is moved to the lower left corner of the top right presentation area of the illustrated series display container. Assuming that the user continues to hold the left button down while moving the trackball (136, 137, 138), the icon counter (indicated by reference numeral 35 in FIG. 2) is incremented or decremented in response to the trackball motion. The threshold check in step 139 indicates when the trackball has moved far enough to increment to the next value of the icon counter. The icon counter indexes to the portion of the object list which contains the image manipulation icons. These objects are numbered consecutively in the object list so that, by constraining the icon counter to cycle through a count sequence which corresponds to the index numbers of the icon objects, the user interface and video driver are enabled to correspondingly cycle through the icon shapes at the cursor location. In step 140, the shape of the cursor is changed at its location to the next image manipulation icon shape in sequence.

Figure 14C:
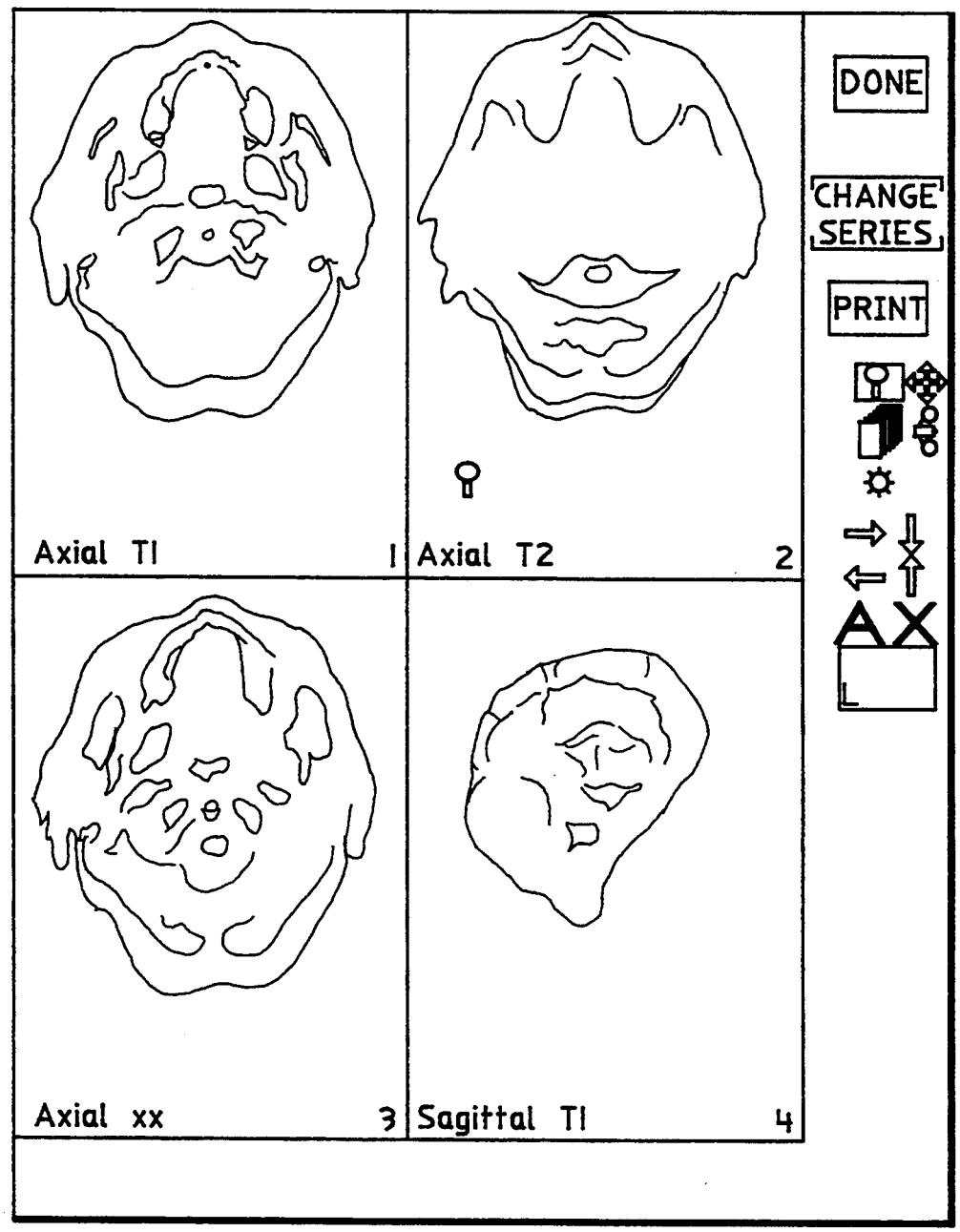
Figure 14D:
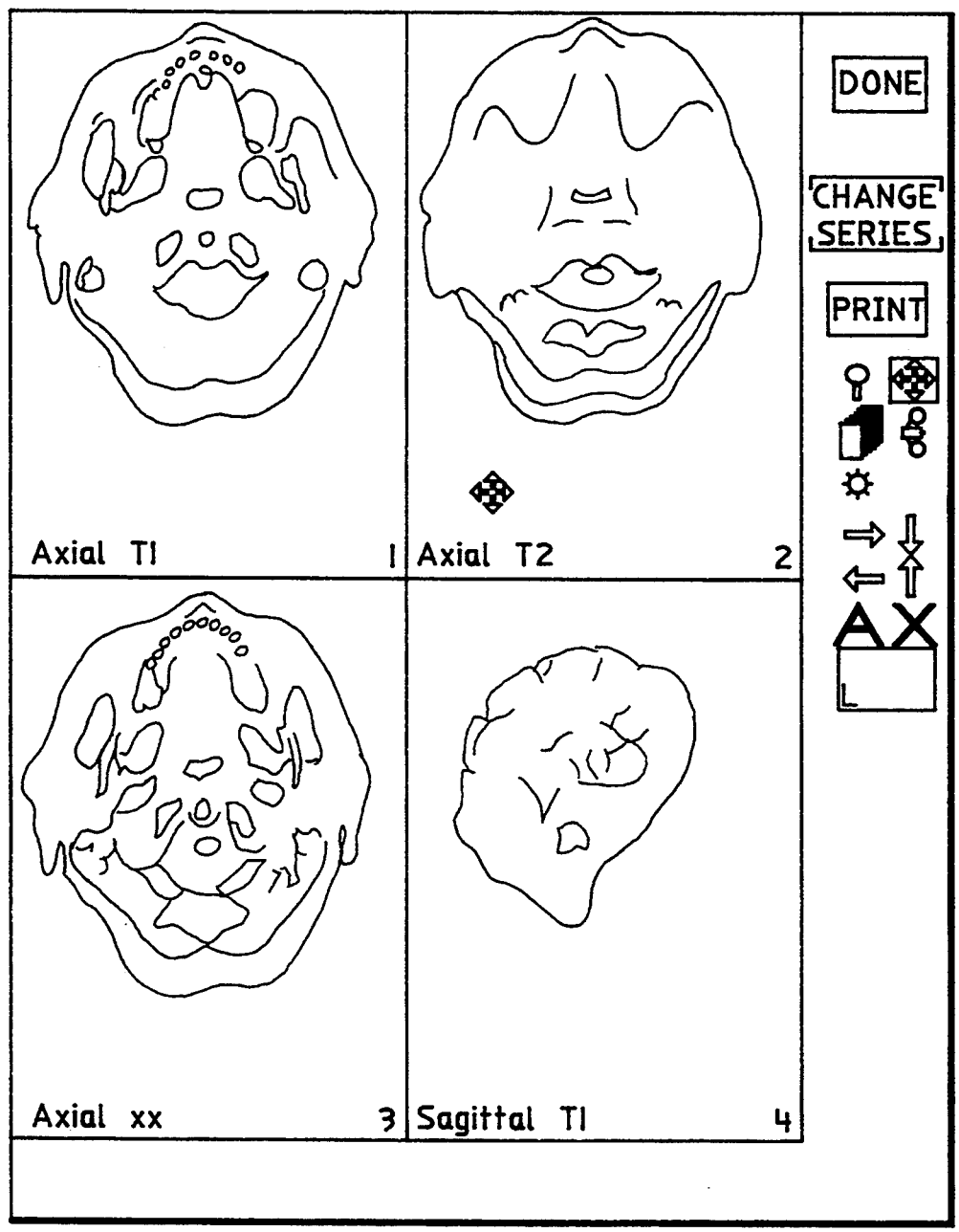

For example, consider FIGS. 14b–14d where the cursor initially has the shape of the riffle icon. Assume that the trackball is moved in a certain direction, resulting in change of the icon counter to a value which corresponds to the magnifying glass icon shape. The result is illustrated in FIG. 14c, where the cursor shape is changed to the magnifying glass. Further movement of the trackball in the same direction results in change at the icon counter to a value corresponding to the image motion icon consisting of four outwardly directed arrows shown in FIG. 14d. As illustrated in step 140, and in FIGS. 14b–14d, each time the cursor shape is changed to that of the next icon in the icon rotation procedure, the corresponding icon is illuminated on the control panel at the cursor location. The decision in step 141 continues the icon rotation loop until the left button is released. In this regard, for so long as the left button is held down and the negative exit is taken from decision 141, the decision at 142 either loops back to the decision 141 if there is no trackball motion or back up to step 138 if there is further trackball motion. If, after icon rotation, the left button is released, the positive exit is taken from decision 141 and a click of the left button is searched for by entering decision 136 through C.

The sequence 136, 137, 145 signifies a left button click to select an icon function, with the function being performed in step 146. This sequence can be entered by selecting an icon shape at the control panel, moving the cursor in the form of the shape to a display container, and then clicking the left button, as at 136, 137, 145. Alternatively, the clicking sequence is detected out of the positive exit from decision 141 after icon rotation when the left button is released. Note that the clicking sequence is exited if trackball motion is detected in step 137 following depression of the left button in step 136 before the left button is released (step 145). Any appropriate reset sequence will restore the cursor to its default shape.

IMAGE ANNOTATION

Image annotation is provided by the set of annotation icons which is beneath the image manipulation icon set in the control panel. Arrows may be dragged from this icon set and selectively dropped on images by moving the cursor to the arrow, clicking the left button to change the shape of the cursor to the arrow, and moving the cursor in the arrow shape to the desired location. At the desired location, clicking the left button will "drop" the arrow at the location. Any appropriate RESET routine will return the cursor to its default shape.

An image can be annotated by selecting the A icon in the control panel, dragging the icon to a location where annotation is desired, clicking the left button of the trackball mechanism and then using the keyboard to annotate the image at the cursor location.

Figure 15:
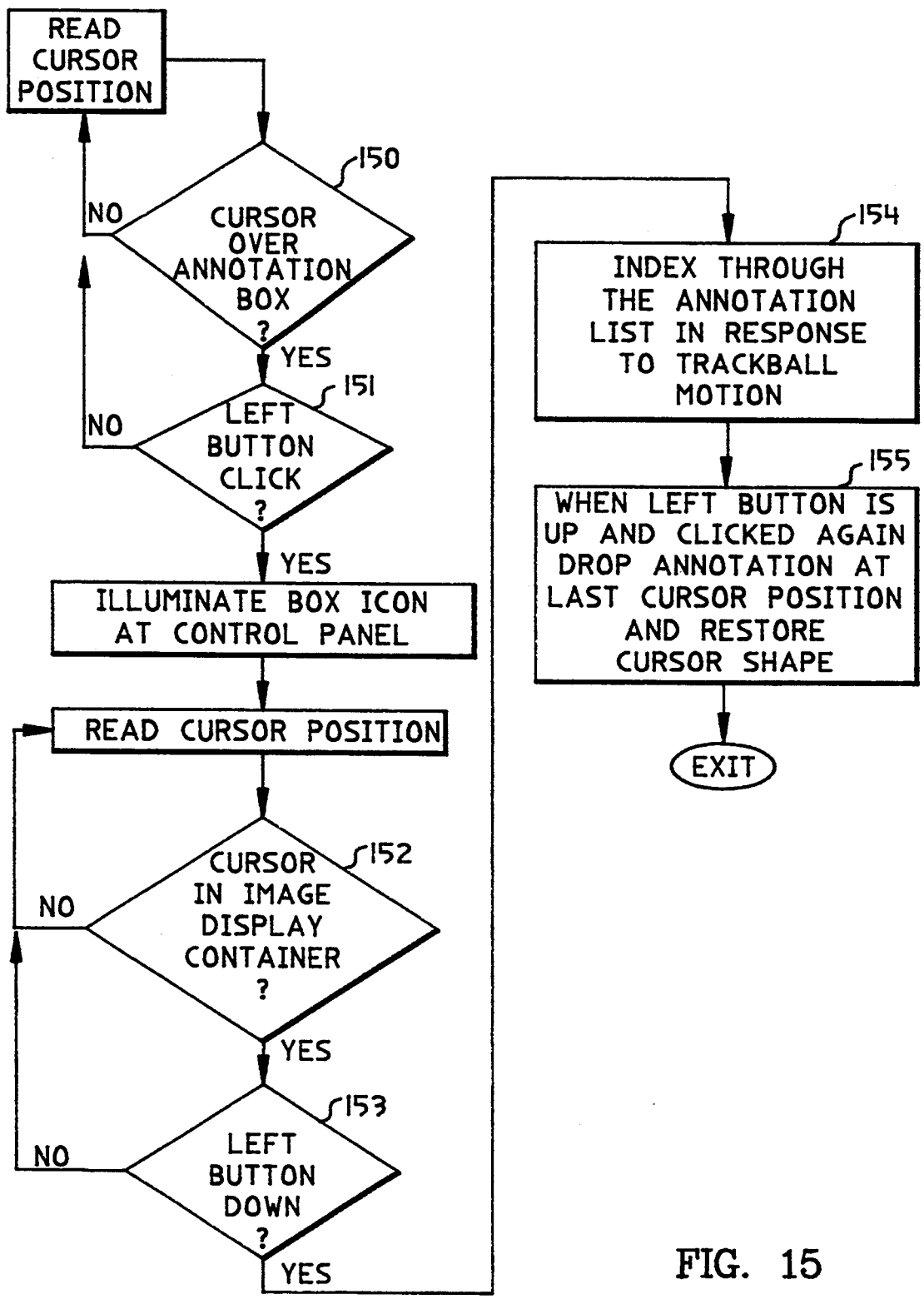
FIG. 15 is a flow diagram illustrating annotation rotation according to the invention.
Figure 16:
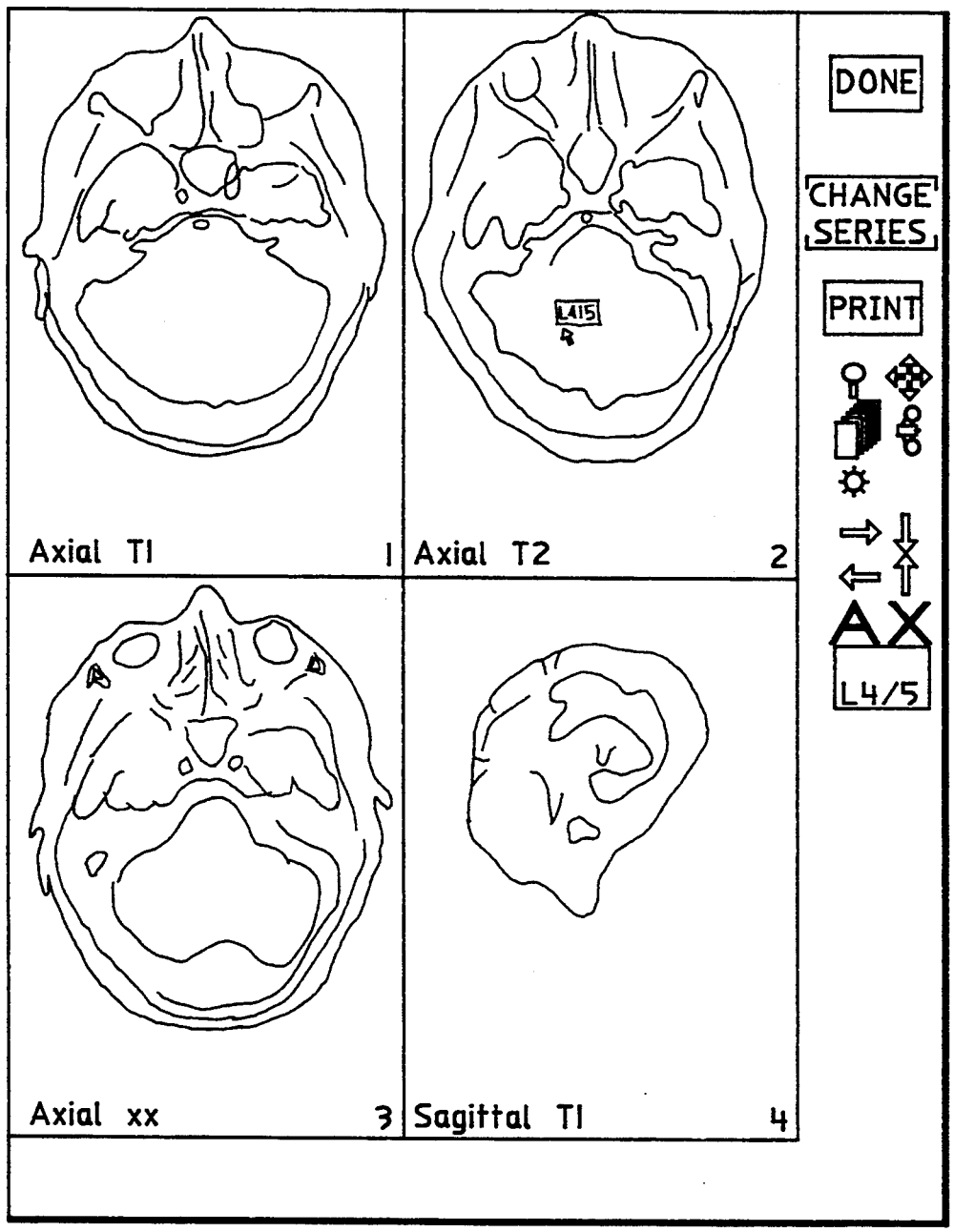
FIG. 16 is an illustration showing a display container with annotation rotation according to the procedure of FIG. 15.
Figure 8:
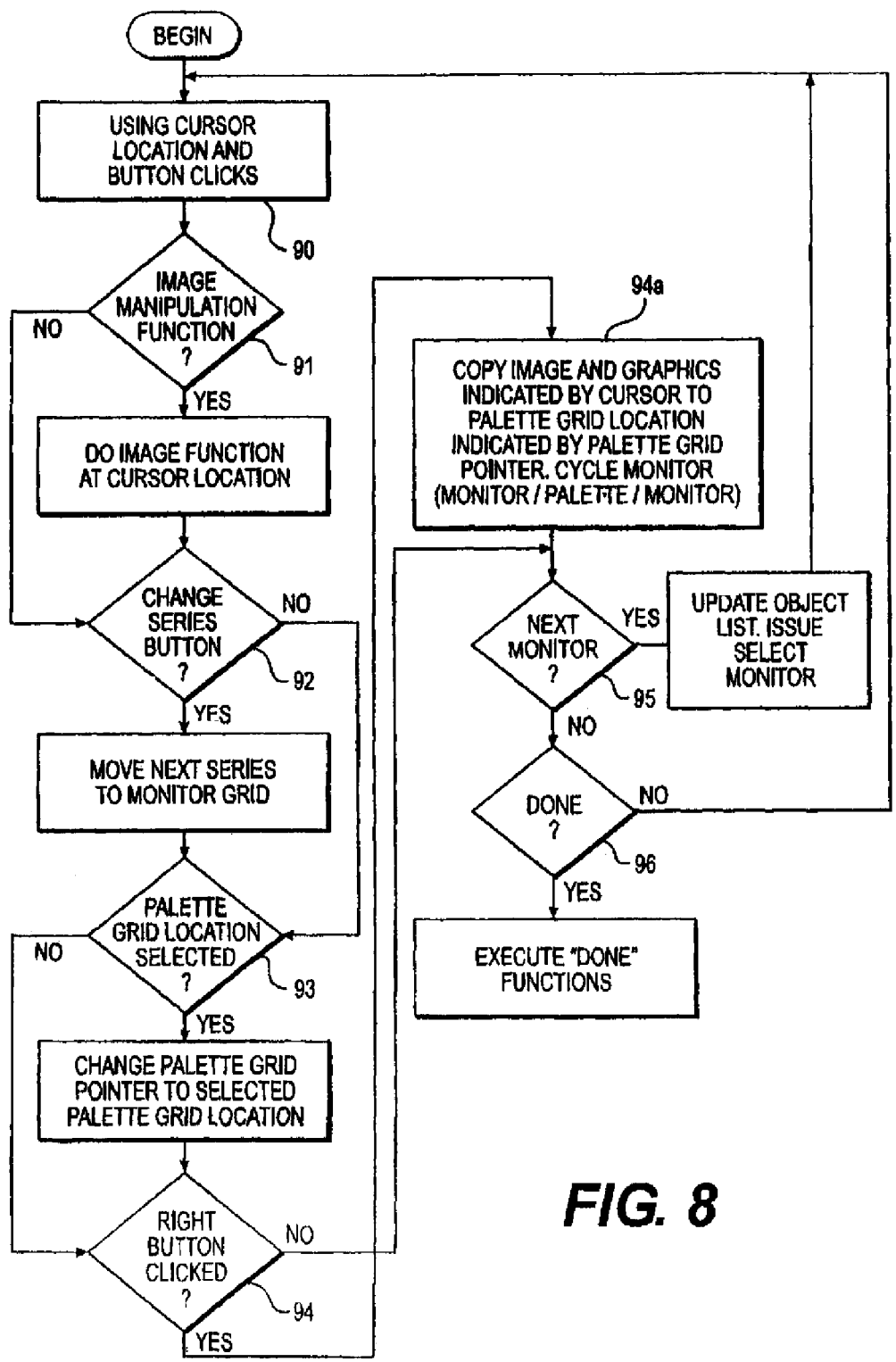

FIGS. 15 and 16 illustrate a procedure executed by the application process for automatically annotating a figure using the annotation lists indicated by reference numeral 60 in FIG. 6. Initially, it is asserted that the application process includes logic capable of selecting an annotation list which is appropriate to the anatomical target. Thus, for example, a sagittal image sequence of a portion of the spine would identify an annotation list which included shorthand annotations commonly employed to identify individual vertebra. The procedure of FIG. 15 provides for the rotation of an annotation list through the annotation box which is illuminated in the annotation icon group in FIG. 16. When this icon is selected, the cursor assumes its shape and is moved in response to the trackball to the desired location. At the desired location, the left button of the trackball is depressed in order to couple the annotation list to the box at the cursor location and in the control panel. For so long as the left button is depressed, motion of the trackball will rotate the listed annotations through the annotation box outlined in the image and in the control panel. When the appropriate annotation is rotated into the box, the left button is released. When the left button is clicked again, the annotation will be dropped in the shape of the annotation box at the cursor location and the cursor's shape will be changed back to the default shape with the tip of the cursor pointing to the lower left-hand corner of the annotation box in the image. This is illustrated in FIG. 16 and the procedure laid out in FIG. 15.

In FIG. 15, when the cursor is clicked at the annotation box, positive exits are taken from decisions 150 and 151, the box icon is illuminated at the control panel and the cursor in the shape of the box is moved to a desired location. When the left button is depressed while the cursor is in an image display container, the positive exits are taken from decisions 152 and 153 and the annotation list is rotated through the box shape in steps 154. When the left button is released and clicked again, the annotation is dropped at the last cursor position and the cursor shape is restored.

The X icon in the annotation set (FIG. 16) is used to delete annotations from an image. Initially, the X icon is clicked using the cursor. This illuminates the X icon and changes the cursor to the icon shape. The cursor is moved over the annotation to be deleted and the left trackball button is clicked. This removes the annotation from the object list and from the image, restores the cursor to its default shape, and turns off the X icon in the control panel.

Clearly, other embodiments and modifications of this invention will occur readily to those of ordinary skill in the art in view of these teachings. For example, cursor movement and clicking can be controlled from a keyboard. Furthermore, the images which are stored in the database may be actual images taken from the human patient, may be images taken from a veterinary subject, or may be synthesized images. Therefore, this invention is to be limited only by the following claims, which include all such embodiments and modifications when viewed in conjunction with the above specification and accompanying drawings.

We claim:

1. A system for presenting images of anatomical structure for examination by a diagnosing physician, including:
    means including one or more display monitors for displaying at least one display container including a display area subdivided into a plurality of presentation areas in a predetermined array;
    means for storing an image database including a plurality of images of anatomical structures, the images being separated into a plurality of image groups, in which:
        each image group is indexed by a unique group identification; and
        each image group is partitioned into one or more ordered image series, each ordered image series including a succession of images which illustrate incrementally registered aspects of an anatomical target, each image series being ordered by assignment to each image in the image series of a numerical position in a respective monotonically changing sequence; and
    physician data tables are stored with indexes to unique group identifications and to physician identifiers and including entries specifying output functions and displaying formats;
    means for receiving a physician identifier;
    means for receiving a group identification;
    means connected to the means for receiving, to the means for storing an image database and to the means for displaying at least one display container and responsive to a physician identification and to a group identification for retrieving at least one image series of an image group indexed by the group identification and for displaying the at least one image series in one or more presentation areas of the plurality of presentation areas in a display format contained in the physician data tables; and
    means for providing an output from the system according to an output function specified in the physician data tables.

2. The system of claim 1, wherein:
    the physician data tables include at least one entry specifying a mode of image series presentation, in which a first mode is a monitor mode and a second mode is a series mode; and
    the means for retrieving and displaying including means for ordering the display of the at least one image series in response to mode specification by:
        displaying each image series of the at least one image series in the order of its respective sequence in a single respective display container in the at least one display container such that each presentation area of the single respective display container includes no more than one image, in response to designation of the monitor mode; and displaying each image series of the at least one image series one image at a time in the order of its respective sequence in a single respective presentation area of the plurality of presentation areas, in response to designation of the series mode.

3. The system of claim 2, further including means for synchronizing the presentation of each image series of two or more image series such that whenever the display of one image series of the two or more image series is changed to display a next image in the order of its respective sequence, each other image series of the two or more image series is correspondingly changed by the means for retrieving and displaying.

4. The system of claim 2, wherein:
the at least one display container includes:
 a first display container for presenting a first plurality of presentation areas in a predetermined array; and
 a second display container for presenting a second plurality of presentation areas in the predetermined array;
the at least one image series includes two or more image series of the image group indexed by the group identification; and
the means for retrieving and displaying displays each image series in the order of its respective sequence in a respective display container such that each presentation area of the respective display container includes no more than one image, in response to designation of the monitor mode of presentation.

5. The system of claim 1, further including:
means for displaying a palette display container on the one or more display monitors, the palette display container for presenting a plurality of presentation areas in an array; and
means for selecting an image of an image series displayed in the at least one display container and reproducing the selected image in a presentation area of the palette display container.

6. A method for presenting images of anatomical structure for examination by a diagnosing physician, the method being executed on a computer display system having:
 a display for displaying at least one display container subdivided into a plurality of presentation areas in a predetermined array;
 a storage subsystem for storing an image database including a plurality of images of anatomical structures; and
 means connected to the storage subsystem and to the at least one display container for retrieving images from the image database and displaying retrieved images in the at least one display container;
the method including the steps of:
 storing a plurality of images in the image database;
 separating the plurality of images into image groups;
 indexing each image group by a unique group identification;
 partitioning each image group into one or more ordered image series, each ordered image series including a succession of images which illustrate incrementally registered aspects of an anatomical target, each image series being ordered by assignment to each image in the image series of a numerical position in a respective monotonically changing sequence;

storing a first data table in the storage subsystem, the first data table listing a plurality of referring physician identifiers, each referring physician identifier being indexed from at least one group identification, each referring physician identifier identifying a referring physician and including respective fields specifying output preferences of the identified referring physician for outputting to the identified referring physician images from the display;
storing a second data table in the storage subsystem, the second data table listing a plurality of diagnosing physician identifiers, each diagnosing physician identifier identifying a diagnosing physician and including respective fields specifying format preferences and mode preferences of the identified diagnosing physician for displaying images on the display; and
providing a group identification;
providing a diagnosing physician identifier;
in response to the group identification and the diagnosing physician identifier, retrieving at least one image series of an image group indexed by the group identification and displaying the at least one image series in one or more presentation areas of the plurality of presentation areas in accordance with a format preference specified in fields of the diagnosing physician identifier; and
outputting images from the at least one image series according to output preferences of a referring physician identified by a referring physician identifier indexed from the group identification.

7. The method of claim 6, further including:
providing mode fields in the diagnosing physician identifiers, each mode field specifying a mode of image series presentation, in which a first mode is a monitor mode and a second mode is a series mode;
displaying one image series in the order of its respective sequence in one display container such that each presentation area of the display container includes no more than one image of the at least one image series, in response to designation of the monitor mode; and
displaying one image series one image at a time in the order of its respective sequence in a single respective presentation area of one display container, in response to designation of the series mode.

8. The method of claim 7, further including the steps of:
displaying a first display container including a first plurality of presentation areas in a predetermined array;
displaying a second display container including a second plurality of presentation areas in the predetermined array;
the step of retrieving and displaying including retrieving two image series of the image group indexed by the group identification; and
the step of retrieving and displaying including displaying each image series in the order of its respective sequence in a respective display container means such that each presentation area of the respective display container means includes one image, in response to designation of the monitor mode of presentation.

9. The method of claim 7, further including the steps of:
in the step of retrieving and displaying, retrieving two image series of the image group indexed by the group identification and displaying each image series one image at a time in the order of its respective sequence in a single respective presentation area.

10. The method of claim 9, further including synchronizing the presentation of each image series of the two image series such that whenever the display of one image series of the two image series is changed to display the next image in the order of its respective sequence, each other image series of the two image series is correspondingly changed.

11. A computer display system for presenting images of anatomical structure for examination, including:
monitor means for presenting graphical images;
means for displaying a first display container and a second display container on the monitor means, the first display container including a first preselected number of substantially rectangular presentation areas in a first substantially rectangular array, and the second display container including a second preselected number of substantially rectangular presentation areas in a second substantially rectangular array;
at least one data storage device for storing:
an image database including a plurality of images of anatomical structure, the images being separated into image groups, in which:
each image group is indexed by a unique group identification, wherein each group identification names a respective image group and includes an identification of a patient whose anatomy is illustrated by the image group; and
each image group is partitioned into one or more ordered image series, each ordered image series including a succession of images which illustrate incrementally registered aspects of an anatomical target, each image series being ordered by assignment to each image in the image series of a position in a respective monotonically changing sequence;
a first table data structure listing a plurality of referring physician identifiers, each referring physician identifier being indexed from at least one group identification, each referring physician identifier identifying a referring physician and including respective fields specifying output preferences of the identified referring physician for outputting to the identified referring physician images from the monitor means; and
a second table data structure listing a plurality of diagnosing physician identifiers, each diagnosing physician identifier identifying a diagnosing physician and including respective fields specifying format preferences and mode preferences of the identified diagnosing physic an for displaying images on the monitor means;
application means connected to the monitor means, to the at least one data storage device and to the means for displaying the first and second display containers and responsive to a user-selected group identification and a diagnosing physician identifier for displaying at least two image series of an image group indexed by the user-selected group identification, said application means further for:
formatting each image series for display on the monitor means in accordance with format preferences specified in fields of the diagnosing physician identifier; displaying each image series on the monitor means in the order of its respective sequence in a respective display container such that each presentation area of the respective display container includes no more than one image; and
outputting images from said at least two image series according to output preferences of a referring physician identified by a referring physician identifier indexed from the user-specified group identification.

12. The computer display system of claim 1, further including:
means for displaying a palette display container on the monitor means, the palette display container including a plurality of presentation areas in an array; and
means coupled to the means for displaying first and second display containers for picking an image of an image series displayed in the first or second display container and reproducing the selected image in a presentation area of the palette display container.

13. The computer display system of claim 1, wherein:
the respective fields of each diagnosing physician identifier specify:
a mode of image series presentation;
a rectangular array format; and
rectangular array dimensions; and
the application means includes respective means for:
presenting an image series in a mode specified by a diagnosing physician identifier;
presenting rectangular arrays in the first and second display containers in a format specified by the diagnosing physician identifier; and
presenting the rectangular arrays in dimensions specified by the diagnosing physician identifier.

14. A computer display system for presenting images of anatomical structure for examination, including:
monitor means for presenting graphical images;
means for displaying at least one display container on the monitor means, the at least one display container including a preselected number of substantially rectangular presentation areas in a substantially rectangular array; and
at least one data storage device for storing:
an image database including a plurality of images of anatomical structure, the images being separated into image groups, in which:
each image group is indexed by a unique group identification, wherein each group identification names a respective image group and includes an identification of a patient whose anatomy is illustrated by the image group; and
each image group is partitioned into one or more ordered image series, each ordered image series including a succession of images which illustrate incrementally registered aspects of an anatomical target, each image series being ordered by assignment to each image in the image series of a position in a respective monotonically changing sequence;
a first table data structure listing a plurality of referring physician identifiers, each referring physician identifier being indexed from at least one group identification, each referring physician identifier identifying a referring physician and including respective fields specifying output preferences of the identified referring physician for outputting to the identified referring physician images from the monitor means; and a second table data structure listing a plurality of diagnosing physician identifiers, each diagnosing physician identifier identifying a diagnosing physician and including respective fields specifying format preferences and mode preferences of the identified diagnosing physician for displaying images on the monitor means;

application means connected to the monitor means, to the at least one data storage device and to the means for displaying at least one display container and responsive to a user-selected group identification and a diagnosing physician identifier for displaying at least two image series of an image group indexed by the user-selected group identification, said application means further for:

formatting each image series for display on the monitor means in accordance with format preferences specified in fields of the diagnosing physician identifier;

displaying each image series on the monitor means one image at a time in the order of its respective sequence in a respective presentation area; and outputting images from said image group according to output preferences of a referring physician identified by a referring physician identifier indexed from the user-specified group identification.

15. The computer display system of claim 2, further including:

means for displaying a palette display container on the monitor means, the palette display container including a plurality of presentation areas in an array; and means coupled to the means for displaying at least one display container for picking an image of an image series displayed in the at least one display container and reproducing the selected image in a presentation area of the palette display container.

16. The computer display system of claim 2, wherein:

the respective fields of each diagnosing physician identifier specify:

a mode of image series presentation;
a rectangular array format; and
rectangular array dimensions; and the application means includes respective means for:

presenting an image series in a mode specified by a diagnosing physician identifier;

presenting rectangular arrays in the at least one display container in a format specified by the diagnosing physician identifier; and presenting the rectangular arrays in dimensions specified by the diagnosing physician identifier.

* * * * *

UNITED STATES PATENT AND TRADEMARK OFFICE
CERTIFICATE OF CORRECTION

PATENT NO.   : 5,452,416
DATED        : September 19, 1995
INVENTOR(S)  : Hilton et al.

It is certified that error appears in the above-indentified patent and that said Letters Patent is hereby corrected as shown below:

Col. 18, lines 36-39, indent the subparagraph rightwardly to align with the subparagraphs beginning at column 18, lines 26 and 28; and line 45, please change "identification" to --identifier--.

Col. 21, line 55, please change "physic " to --physician--;

line 65, indent the subparagraph rightwardly to align with the subparagraphs beginning at column 21, lines 28 and 33; and Col. 21, line 68 through Col. 22, line 4, please make a subparagraph break between the semicolon and "displaying" and align the subparagraph:

displaying each image series on the monitor means in
    the order of its respective sequence in a respective
    display container such that each presentation area of
    the respective display container includes no more than
    one image; and with the subparagraphs beginning at Col. 21, lines 28 and 33.

Col. 22, lines 10 and 23, change each occurrence of "1" to --11--.

UNITED STATES PATENT AND TRADEMARK OFFICE
CERTIFICATE OF CORRECTION

PATENT NO. : 5,452,416
DATED : September 19, 1995
INVENTOR(S) : HIlton, et al.

It is certified that error appears in the above-indentified patent and that said Letters Patent is hereby corrected as shown below:

Col. 24, lines 3 and 15, change each occurrence of "2" to --14--.

Signed and Sealed this

Twenty-seventh Day of February, 1996

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,452,416
APPLICATION NO. : 07/998550
DATED : September 19, 1995
INVENTOR(S) : Wesley W. Hilton et al.

It is certified that error appears in the above-identified patent and that said Letters Patent is hereby corrected as shown below:

The sheet of drawing consisting of figure 8 should be deleted to appear as per attached figure 8.

Signed and Sealed this

Thirty-first Day of March, 2009

JOHN DOLL
*Acting Director of the United States Patent and Trademark Office*

US005452416C1

(12) EX PARTE REEXAMINATION CERTIFICATE (8173rd)

United States Patent
Hilton et al.

(10) Number: US 5,452,416 C1
(45) Certificate Issued: Apr. 26, 2011

(54) AUTOMATED SYSTEM AND A METHOD FOR ORGANIZING, PRESENTING, AND MANIPULATING MEDICAL IMAGES

(75) Inventors: Wesley W. Hilton, Del Mar, CA (US); Murray A. Reicher, Rancho Santa Fe, CA (US); Dale Seegmiller, Solana Beach, CA (US)

(73) Assignee: D.R. Systems, Inc., San Diego, CA (US)

Reexamination Request:
No. 90/010,393, Jan. 23, 2009

Reexamination Certificate for:
Patent No.: 5,452,416
Issued: Sep. 19, 1995
Appl. No.: 07/998,550
Filed: Dec. 30, 1992

Certificate of Correction issued Feb. 27, 1996.

Certificate of Correction issued Mar. 31, 2009.

(51) Int. Cl.
*G06F 19/00* (2006.01)

(52) U.S. Cl. .................. 715/783; 715/792; 715/854; 715/968; 345/424

(58) Field of Classification Search .................. None
See application file for complete search history.

(56) References Cited

U.S. PATENT DOCUMENTS

| | | |
|---|---|---|
| 4,653,021 A | 3/1987 | Takagi |
| 4,680,643 A | 7/1987 | Horiguchi |
| 4,817,050 A | 3/1989 | Komatsu et al. |
| 4,833,625 A | 5/1989 | Fisher et al. |
| 5,019,975 A | 5/1991 | Mukai |
| 5,027,110 A | 6/1991 | Chang et al. |
| 5,086,392 A | 2/1992 | Nakajima |
| 5,119,492 A | 6/1992 | Shimizu et al. |
| 5,140,518 A | 8/1992 | Ema |
| 5,202,996 A | 4/1993 | Sugino et al. |
| 5,414,834 A | 5/1995 | Alexander et al. |
| 5,452,416 A | 9/1995 | Hilton et al. |

OTHER PUBLICATIONS

Kim, et al. "Technology Requirement for Functional PACS Workstations," Proceedings of Technology Requirements for Biomedical Imaging, IEEE Computer Society Press, pp. 111–116, May 21–22, 1991.*

"Medical Diagnostic Imaging Support (MDIS) System—Response to Government Questions," Ford Aerospace (Loral), Mar. 19, 1991.

"Response to the Performance Work Statement for a Medical Diagnostic Imaging System," Siemens, Apr. 20, 1990.

(Continued)

*Primary Examiner*—Zoila E Cabrera

(57) ABSTRACT

An automated system for organizing, presenting, and manipulating medical images includes a database in which the medical images are structured into groups, each group including one or more image series, each image series including an ordered sequence of images which illustrate incrementally registered aspects of an anatomical target. Image series are presented in their sequential order either in a monitor presentation format which displays each sequence in its entirety in a single monitor display container or which presents two or more image series, image-by-image, in adjacent presentation areas of a series display container. The system includes a plurality of monitors in which all monitors, save one, produce display containers for image series presentation. One monitor is reserved for displaying a working palette to which images of the image series displayed on the other monitors may be moved. The system activates a monitor in a plurality of monitors in response to movement of a cursor between monitors. An active monitor is indicated by presentation of a control panel. The system also provides heads-up presentation of control panel icons at a cursor location outside of the control panel by sequentially changing the shape of the cursor to the icon shapes for user selection.

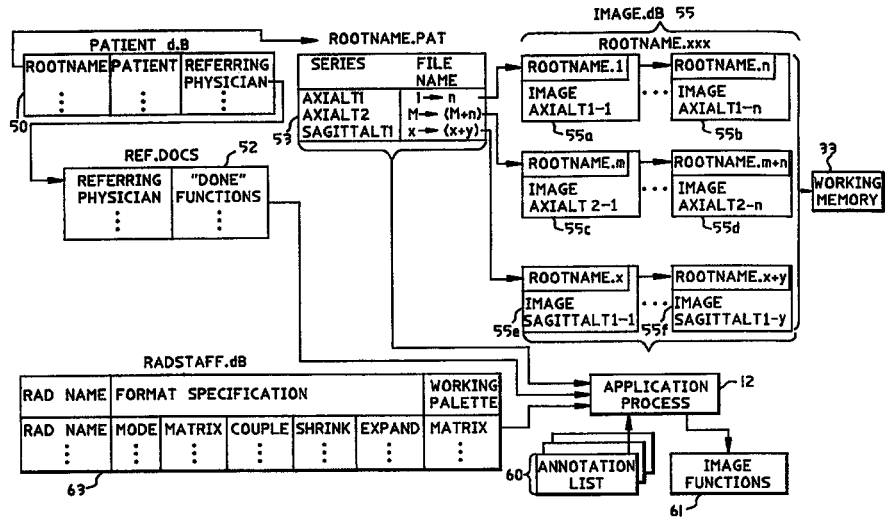

OTHER PUBLICATIONS

"Medical Diagnostic Imaging Support (MDIS) System," Ford Aerospace (Loral), Oct. 26, 1990.

"The Desktop Workstation Litebox," Siemens brochure, Nov. 1990.

"Operating Instructions Litebox, Revision B," Siemens, Dec. 1991.

Haynor, D., et al., "Clinical Evaluations of PACS Workstations—Methodology and Results," Medical Imaging IV: PACS Systems Design and Evaluation, SPIE vol. 1234, pp. 408–417 (1990).

Smith, D.V., et al., "MDIS Workstation Issues: Clinical Perspective," Image Capture, Formatting and Display, SPIE vol. 1444, pp. 357–362 (1991).

"The IARS User Manual," Vortech Data, Inc., Nov. 1991.

"Vortech Personal Display System Product Specification, II," Vortech Data, Inc., Jun. 28, 1990.

"Personal Display System User Guide," Vortech Data Inc., Jun. 1991.

"Apex 409AG Operation Manual," Elscint Ltd., Mar. 1985.

Wendler, T., et al., "Digital Imaging Workstations," Hospital Integrated Picture Archiving and Communications Systems—A Second Generation PACS Concept, pp. 173–210 (1992).

Levin, K., "Functional Diagnostic Specifications for an Intelligent Radiology Workstation," Computer Applications to Assist Radiology (1990).

Wendler, T., "Cooperative Human–Machine Interfaces for Medical Image Workstations: A Scenario," Int. Symp. on Computer Assisted Radiology, pp. 775–779 (1989).

Wendler, T., et al., "Design Considerations for Multi Modality Medical Image Workstations," Pictorial Information Systems in Medicine, Proc. of the NATO Advanced Study Institute, NATO–ASI Series F, Computer and Systems Sciences, vol. 19, pp. 401–420 (1986).

Wendler, T., et al., "A Rule–Based Model of Diagnostic Information Requirements for the Design Adaptive Image Workstations," Symp. On Computer Assisted Radiology, pp. 629–635 (1991).

Arneson, R., et al., "The Digital Imaging Workstation," Radiology, vol. 176. No. 2, pp. 303–315, Aug. 1990.

Ho, B., et al., "PACS Workstation Design," Computerized Medical Imaging and Graphics, vol. 15, No. 3, pp. 147–155, May–Jun. 1991.

Hedgcock, M., et al., "Database Requirements for PACS," Medical Imaging IV: PACS System Design and Evaluation, SPIE vol. 1234, pp. 588–592 (1990).

Robb, R.B., et al., "A Software System for Interactive and Quantitative Analysis of Biomedical Images," Australian Phys. & Enigrg. Sciences in Medicine, vol. 14, pp. 9–30, Nov. 1990.

Mattheus, R. et al. "Differentiation and Requirements of Image–Computers in a Clinical PACS Environment," ISCAMI1: Integrated System for the Management and Manipulation of Medical Images, pp. 36–45 (1989).

Freeman, R., et al., "Operator Interface Design for a PACS Primary Diagnosis Workstation," Medical Imaging IV: PACS System Design and Evaluation, SPIE vol. 1234, pp. 430–441 1990.

Lugier, Y., et al., "The OSIRIS User Interface for Manipulating Medical Images," Picture Archiving and Communication Systems (PACS) in Medicine, NATO ASI Series, vol. F74, pp. 395–398 (1991).

Zeleznik, M., et al., "PACS Data Base Design," Picture Archiving and Communication System (PACS II) for Medical Applications, SPIE vol. 418, pp. 287–295 (1983).

Ratib, O., et al., "PACS Workstation: User Interface Design," Picture Archiving and Communication Systems (PACS) in Medicine, NATO ASI Series, vol. F74, pp. 57–61 (1991).

Janjua, A., et al., "A Multimodality Image Display and Image Processing System," Picture Archiving and Communication System (PACS III) for Medical Applications, SPIE vol. 536, pp. 165–168 (1985).

Massicottee, J., et al., "A Menu–Driven User Interface for a Physician's Imaging Console," Picture Archiving and Communication System (PACS III) for Medical Applications, SPIE vol. 536, pp. 158–164 (1985).

Steinke, J., et al., "Operator Interface Design Considerations for a PACS Information Management System," Medical Imaging IV: PACS System Design and Evaluation, SPIE vol. 1234, pp. 444–453 (1990).

"A Software System for Interactive and Quantitative Analysis of Biomedical Images," 3D Imaging in Medicine, NATO ASI Series, vol. F60, pp. 333–410 (1990).

Greinacher, C.F.C., et al., "A Detailed RIS/PACS Interface Specification Based on the Marburg Model," Lecture notes in medical informatics No. 37, Springer Verlag, pp. 39–88 (1988).

Hruby, W., et al., "The Vienna SMZO–PACS Project: The Totally Digital Hospital," Computer Assisted Radiology, Proceedings of the International Symposium, 436–441 (1991).

Mosser, H., et al., "The Vienna SMZO Project," Picture Archival Communications Systems (PACS) in Medicine, NATO ASI Series, vol. F74, pp. 247–259 (1991).

Wirsz, E., et al., "Validation Driven Modeling of a PACS Database in a Shared File System Environment," PACS Design and Evaluation, SPIE vol. 1899, pp. 144–156 (1993).

Erradi, et al., "Visual Interaction Using an Iconic System," The Visual Computer, vol. 4, No. 98, pp. 98–103 (1983).

Kim, Y., et al., "A NeXT–Based High Performance Image Computing Workstation for Biomedical Applications," Annual Int'l Conf. of IEEE Engineering in Medicine and Biology Soc., vol. 12, No. 1, pp. 219–220 (1990).

Sanders, J., et al., "Design and Implementation of a Clinical MSI Workstation," Proc. 5th Annula IEEE Symposium on Computer–Based Medical Systems, pp. 138–146 (1992).

Smith, D.V., et al., "Design Strategy and Implementation of the Medical Diagnostic Image Support System at Two Large Military Medical Centers," Proceedings of SPIE— vol. 1654 Medical Imaging VI: PACS Design and Evaluation, Jul. 1992, pp. 148–157.

Smith, D., "Design and Implementation Strategy for a Filmless Hospital in The U.S. Military Medical Establishment," 2nd Int'l Conf. on Image Management and Communication (IMAC) in Patient Care: New Technologies for Better Patient Care, Apr. 1991, pp. 195–198.

Wirtz, et al., "Hierarchical Rapid Modeling of Picture Archiving and Communication Systems Using LANNET II.5 and Network II.5," Proceedings of the 1992 Winter Simulation Conf., Dec. 1992, pp. 1356–1364.

Haynor, D.R., et al., "Hardware and Software Requirements for a Picture Archiving and Communication System's Diagnostic Workstations," Journal of Digital Imaging, vol. 5, No. 2, May 1992, pp. 107–117.

Leckie, R.G., et al., "Early Evaluation of MDIS Workstations at Madigan Army Medical Center," SPIE vol. 1897 Image Capture, Formatting, and Display (1993), pp. 336–349.

Relevant portions of the '416 patent file history.

Medical Diagnostic Imaging Support System, Specification: issued by the US Army Engineering Division, Huntsville, Alabama, Solicitation #DACA87–90–R–0058, Amendment 0009, Jun. 14, 1991.

Kim, et al. "Technology Requirement for Functional PACS Workstations," Proceedings of Technology Requirements for Biomedical Imaging, IEEE Computer Society Press, pp. 111–116 (May 1991).

"Digital Imaging and Communications," ACR/NEMA Standards Publication No. 300–1988, National Electrical Manufacturers Association (1988).

Original Civil Complaint filed in the District Court for the Northern District of Illinois for *DR Systems, Inc.* v. *Lake Forest Hospital*, Civil Action No. 1:08–cv–05878.

Original Civil Complaint filed in the District Court for the Southern District of California for *DR Systems, Inc.* v. *Emageon Inc. et al.*, Civil Action No. 3:08–cv–01732.

Joint Claim Construction Chart filed on Dec. 12, 2006, in *DR Systems, Inc.* v. *Fujifilm Medical Systems USA, Inc. et al.*, United States District Court for the Southern District of California, Case No. 1:06–cv–0417.

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-16 are cancelled.

New claims 17-33 are added and determined to be patentable.

*17. A system for presenting image of anatomical structure for examination by a diagnosing physician, including:*
  *means including one or more display monitors for displaying at least one display container including a display area subdivided into a plurality of presentation areas in a predetermined array;*
  *means for storing an image database including a plurality of images of anatomical structures, the images being separated into a plurality of image groups, in which:*
    *each image group is indexed by a unique group identification; and*
    *each image group is partitioned into at least two ordered image series, each ordered image series including a succession of images which illustrate incrementally registered aspects of an anatomical target, each image series being ordered by assignment to each image in the image series of a numerical position in a respective monotonically changing sequence; and*
    *diagnosing physician data tables are stored with indexes to unique group identifications and to diagnosing physician identifiers and including entries specifying output functions and displaying formats;*
  *means for receiving a diagnosing physician identifier;*
  *means for receiving a group identification;*
  *means connected to the means for receiving, to the means for storing an image database and to the means for displaying at least one display container and responsive to a received diagnosing physician identifier and to a received group identification for retrieving at least one image series of an image group indexed by the group identification and for displaying the at least one image series in one or more presentation areas of the plurality of presentation areas in a displaying format contained in the diagnosing physician data tables, wherein the displaying formats include (a) a monitor mode in which multiple images from at least one image series are displayed with each image in a respective presentation area and (b) a series mode in which one image from each of at least two image series is displayed with each image in a respective presentation area and in which a diaplayed image can be changed by a user command to display in the same presentation area a different image in the same image series; and*
  *means for providing an output from the system according to an output function specified in the diagnosing physician data tables, wherein the output function effects display of images from an image group indexed by the received group identification in the monitor mode or the series mode in accordance with the received diagnosing physician identifier.*

*18. The system of claim 17, wherein the presentation of images from different image series in the series mode is synchronized such that whenever the display of an image in one presentation area is changed to display a different image in a particular numerical position in its sequence of images, a displayed image in another presentation area is correspondingly changed to display an image in the same numerical position in its sequence of images.*

*19. The system of claim 18, wherein the user command in the series mode changes the displayed image to the next image in the order of its sequence in the image series.*

*20. The system of claim 17, wherein the user command in the series mode changes the displayed image to the next image in the order of its sequence in the image series.*

*21. A system for presenting images of structure for anatomical examination by a diagnosing physician, including:*
  *means including one or more display monitors for displaying at least one display container including a display area subdivided into a plurality of presentation areas in a predetermined array;*
  *means for storing an image database including a plurality of images of anatomical structures, the images being separated into a plurality of image groups, in which;*
    *each image group is indexed by a unique group identification; and*
    *each image group is partitioned into at least two ordered image series, each ordered image series including a succession of images which illustrate incrementally registered aspects of an anatomical target, each image series being ordered by assignment to each image in the image series of a numerical position in a respective monotonically changing sequence; and*
    *diagnosing physician data tables are stored with indexes to unique group identifications and to diagnosing physician identifiers and including entries specifying output functions and displaying formats;*
  *means for receiving a diagnosing physician identifier;*
  *means for receiving a group identification;*
  *means connected to the means for receiving, to the means for storing an image database and to the means for displaying at least one display container and responsive to a received diagnosing physician identifier and to a received group identification for retrieving at least one image series of an image group indexed by the group identification and for displaying the at least one image series in one or more presentation areas of the plurality of presentation areas in a displaying format contained in the diagnosing physician data tables, wherein the displaying formats include a series mode in which one image from each of at least two image series is displayed with each image in a respective presentation area and in which a displayed image can be changed by a user command to display in the same presentation area a different image in the same image series; and*
  *means for providing an output from the system according to an output function specified in the diagnosing physician data tables,*
  *wherein the presentation of images from different image series in the series mode is synchronized such that* whenever the display of an image in one presentation area is changed to display a different image in a particular numerical position in its sequence of images, a displayed image in another presentation area is correspondingly changed to display an image in the same numerical position in its sequence of images.

22. The system of claim 21, wherein the user command in the series mode changes the displayed image to the next image in the order of its sequence in the image series.

23. A system for presenting images of anatomical structure for examination by a diagnosing physician, including:
   a display including one or more display monitors for displaying at least one display container including a display area subdivided into a plurality of presentation areas in a predetermined array;
   a storage device storing an image database including a plurality of images of anatomical structures, the images being separated into a plurality of image groups, in which:
      each image group is indexed by a unique group identification; and
      each image group is partitioned into at least two ordered image series, each ordered image series including a succession of images which illustrate incrementally registered aspects of an anatomical target, each image series being ordered by assignment to each image in the image series of a numerical position in a respective monotonically changing sequence; and
      diagnosing physician data tables are stored with indexes to unique group identifications and to diagnosing physician identifiers and including entries specifying output functions and displaying formats;
   at least one input device for receiving a diagnosing physician identifier and a group identification; and
   a computer processor connected to the input device, the storage device and the display and responsive to a received diagnosing physician identifier and to a received group identification for retrieving at least one image series of an image group indexed by the group identification and for displaying the at least one image series in one or more presentation areas of the plurality of presentation areas in a displaying format contained in the diagnosing physician data tables, wherein the displaying formats include (a) a monitor mode in which multiple images from at least one image series are displayed with each image in a respective presentation area and (b) a series mode in which one image from each of at least two image series is displayed with each image in a respective presentation area and in which a displayed image can be changed by a user command to display in the same presentation area a different image in the same image series,
   said computer processor providing an output from the system according to an output function specified in the diagnosing physician data tables, wherein the output function effects display of images from an image group indexed by the received image identification in the monitor mode or the series mode in accordance with the received physician identifier.

24. The system of claim 23, wherein the presentation of images from different image series in the series mode is synchronized such that whenever the display of an image in one presentation area is changed to display a different image in a particular numerical position in its sequence of images, a displayed image in another presentation area is correspondingly changed to display an image in the same numerical position in its sequence of images.

25. The system of claim 24, wherein the user command in the series mode changes the displayed image to the next image in the order of its sequence in the image series.

26. The system of claim 23, wherein the user command in the series mode changes the displayed image to the next image in the order of its sequence in the image series.

27. A system for presenting images of anatomical structure for examination by a diagnosing physician, including:
   a display including one or more display monitors for displaying at least one display container including a display area subdivided into a plurality of presentation areas in a predetermined array;
   a storage device storing an image database including a plurality of images of anatomical structures, the images being separated into a plurality of image groups, in which:
      each image group is indexed by a unique group identification; and
      each image group is partitioned into at least two ordered image series, each ordered image series including a succession of images which illustrate incrementally registered aspects of an anatomical target, each image series being ordered by assignment to each image in the image series of a numerical position in a respective monotonically changing sequence; and
      diagnosing physician data tables are stored with indexes to unique group identifications and to diagnosing physician identifiers and including entries specifying output functions and displaying formats;
   at least one input device for receiving a diagnosing physician identifier and a group identification; and
   a computer processor connected to the input device, the storage device and the display and responsive to a received diagnosing physician identifier and to a received group identification for retrieving at least one image series of an image group indexed by the group identification and for displaying the at least one image series in one or more presentation areas of the plurality of presentation areas in a displaying format contained in the diagnosing physician data tables, wherein the displaying formats include a series mode in which one image from each of at least two image series is displayed with each image in a respective presentation area and in which a displayed image can be changed by a user command to display in the same presentation area a different image in the same image series,
   said computer processor providing an output from the system according to an output function specified in the diagnosing physician data tables,
   wherein the presentation of images from different image series in the series mode is synchronized such that whenever the display of an image in one presentation area is changed to display a different image in a particular numerical position in its sequence of images, a displayed image in another presentation area is correspondingly changed to display an image in the same numerical position in its sequence of images.

28. The system of claim 27, wherein the user command in the series mode changes the displayed image to the next image in the order of its sequence in the image series.

29. A system for presenting images of anatomical structure for examination by a diagnosing physician, including:
   means including one or more display monitors for displaying at least one display container including a display area subdivided into a plurality of presentation areas in a predetermined array;

means for storing an image database including a plurality of images of anatomical structures, the images being separated into a plurality of image groups, in which:

each image group is indexed by a unique group identification; and each image group is partitioned into one or more ordered image series, each ordered image series including a succession of images which illustrate incrementally registered aspects of an anatomical target, each image series being ordered by assignment to each image in the image series of a numerical position in a respective monotonically changing sequence; and physician data tables are stored with indexes to unique group identifications and to physician identifiers and including entries specifying output functions and displaying formats;

means for receiving a physician identifier;

means for receiving a group identification;

means connected to the means for receiving, to the means for storing an image database and to the means for displaying at least one display container and responsive to a physician identifier and to a group identification for retrieving at least one image series of an image group indexed by the group identification and for displaying the at least one image series in one or more presentation areas of the plurality of presentation areas in a display format contained in the physician data tables; and means for providing an output from the system according to an output function specified in the physician data tables, wherein one of the output functions comprises a DONE function that effects delivery of images to a referring physician in response to a user command entered by the diagnosing physician.

30. *A system for presenting images of anatomical structure for examination by a diagnosing physician, including:*

*means including one or more display monitors for displaying at least one display container including a display area subdivided into a plurality of presentation areas in a predetermined array;*

*means for storing an image database including a plurality of images of anatomical structures, the images being separated into a plurality of image groups, in which:*

*each image group is indexed by a unique group identification; and*

*each image group is partitioned into one or more ordered image series, each ordered image series including a succession of images which illustrate incrementally registered aspects of an anatomical target of a patient referred by a referring physician for examination, each image series being ordered by assignment to each image in the image series of a numerical position in a respective monotonically changing sequence; and*

*physician data tables are stored with indexes to unique group identifications and to diagnosing physician identifiers and including entries specifying output functions and displaying formats, wherein the output functions effect image displaying formats in accordance with diagnosing physician preferences and delivery of images in accordance with referring physician preferences indexed from the group identifications;*

*means for receiving a diagnosing physician identifier;*

*means for receiving a group identification;*

*means connected to the means for receiving, to the means for storing an image database and to the means for displaying at least one display container and responsive to a received diagnosing physician identifier and to a received group identification for retrieving at least one image series of an image group indexed by the group identification and for displaying the at least one image series in one or more presentation areas of the plurality of presentation areas in a display format contained in the physician data tables; and*

*means for providing an output from the system according to an output function specified in the physician data tables associated with a referring physician preference indexed from the received group identification, wherein the output function determines the manner of delivering images to a referring physician and delivers the images in response to a user command entered by the diagnosing physician.*

31. *The system of claim 30, wherein the manner of delivering the images includes at least one of printing a hard copy of a displayed image or electronically sending a displayed image to a predetermined location.*

32. *A system for presenting images of anatomical structure for examination by a diagnosing physician, including:*

*a display including one or more display monitors for displaying at least one display container including a display area subdivided into a plurality of presentation areas in a predetermined array;*

*a storage device storing an image database including a plurality of images of anatomical structures, the images being separated into a plurality of image groups, in which:*

*each image group is indexed by a unique group identification; and*

*each image group is partitioned into one or more ordered image series, each ordered image series including a succession of images which illustrate incrementally registered aspects of an anatomical target of a patient referred by a referring physician for examination, each image series being ordered by assignment to each image in the image series of a numerical position in a respective monotonically changing sequence; and*

*physician data tables are stored with indexes to unique group identifications and to diagnosing physician identifiers and including entries specifying output functions and displaying formats, wherein the output functions effect image displaying formats in accordance with diagnosing physician preferences and delivery of images in accordance with referring physician preferences indexed from the group identifications;*

*at least one input device for receiving a diagnosing physician identifier and a group identification; and*

*a computer processor connected to the input device, the storage device and the display and responsive to a received diagnosing physician identifier and to a received group identification for retrieving at least one image series of an image group indexed by the group identification and for displaying the at least one image series in one or more presentation areas of the plurality of presentation areas in a display format contained in the physician data tables,*

*said computer processor providing an output from the system according to an output function specified in the*

*physician data tables associated with a referring physician preference indexed from the received group identification, wherein the output function determines the manner of delivering images to a referring physician and delivers the images in response to a user command entered by the diagnosing physician.*

*33. The system of claim 32, wherein the manner of delivering the images includes at least one of printing a hard copy of a displayed image or electronically sending a displayed image to a predetermined location.*

\* \* \* \* \*